(12) United States Patent
Yu et al.

(10) Patent No.: US 8,017,642 B2
(45) Date of Patent: Sep. 13, 2011

(54) FUNCTIONALLY SELECTIVE ALPHA2C ADRENORECEPTOR AGONISTS

(75) Inventors: Younong Yu, East Brunswick, NJ (US); Pietro Mangiaracina, Monsey, NY (US); Kevin D. McCormick, Basking Ridge, NJ (US); Christopher W. Boyce, Flemington, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 12/525,648

(22) PCT Filed: Feb. 11, 2008

(86) PCT No.: PCT/US2008/001808
§ 371 (c)(1),
(2), (4) Date: Mar. 1, 2010

(87) PCT Pub. No.: WO2008/100480
PCT Pub. Date: Aug. 21, 2008

(65) Prior Publication Data
US 2010/0144816 A1 Jun. 10, 2010

Related U.S. Application Data

(60) Provisional application No. 60/901,064, filed on Feb. 13, 2007.

(51) Int. Cl.
*A61K 31/4164* (2006.01)
*C07D 233/64* (2006.01)
(52) U.S. Cl. ..................... 514/400; 548/335.1
(58) Field of Classification Search .................. 514/400; 548/335.1
See application file for complete search history.

(56) References Cited

U.S. PATENT DOCUMENTS

| 5,658,938 | A | 8/1997 | Geerts et al. |
| 6,841,684 | B2 | 1/2005 | Chow et al. |
| 2003/0023098 | A1 | 1/2003 | Chow et al. |
| 2007/0093477 | A1 | 4/2007 | McCormick et al. |
| 2007/0099872 | A1 | 5/2007 | McCormick et al. |
| 2008/0027100 | A1 | 1/2008 | McCormick et al. |

FOREIGN PATENT DOCUMENTS

| EP | 0 0445 073 A | 9/1991 |
| EP | 1 170 288 A | 1/2002 |
| WO | WO 97/12874 | 4/1997 |
| WO | WO 99/28300 | 6/1999 |
| WO | WO 01/00586 | 1/2001 |
| WO | WO 02/076950 | 10/2002 |
| WO | WO 03/099795 | 12/2003 |
| WO | WO 2005/005781 | 1/2005 |
| WO | WO 2007/085556 | 8/2007 |
| WO | WO 2008/100456 A2 | 8/2008 |
| WO | WO 2008/100459 A1 | 8/2008 |
| WO | WO 2008/100463 A1 | 8/2008 |
| WO | WO 2008/100480 A1 | 8/2008 |

OTHER PUBLICATIONS

Ahlquist RP, "A Study of the Adrenotropic Receptors," Am. J. Physiol., (1948), pp. 586-600, vol. 153.
Bagley et al., "Synthesis and Alpha.2-adrenergic Activities of Imidazole and Imidazolidine analogues, in Vivtro and in Vivo Selectivity", Medicinal Chemistry Research, Birkhauser, Boston, US, (1994), pp. 346-364, vol. 4 No. 5.
Bousquet et al., "Role of the Ventral Surface of the Brain Stem in the Hypotensive Action of Clonidine", European Journal of Pharmacology, (1975), pp. 151-156, vol. 34.
Bousquet, P. et al., "Imidazoline Receptors: From Basic Concepts to Recent Developments", Journal of Cardiovascular Pharmacology, (1995), pp. S1-S6, (Suppl. 2). vol. 26.
Hong et al., "A Structure-Activity Relationship Study of Benzylic Modification of 4-[1-(1-Naphtyl)ethyl]-1H-imidazoles on α-2-Adrenergic Receptors", J. Med. Chem., (1994) pp. 2328-2333, vol. 37 No. 15.
Lalchandani et al., "Medetomidine analogs as selective agonists for the human α2-adrenoceptors", Biochemical Pharmacology, (2004), pp. 87-96, vol. 67, No. 1 XP002472947.
Lands et al., "Differentiation of Receptor Systems Activated by Sympathomimetic Amines", Nature, (1967), pp. 597-598, vol. 214.
MacDonald et al., "Gene Targeting—Homing in on Alpha2-Adrenoceptor-Subtype Function", TiPS, (1997), pp. 211-219, vol. 18.
Michel et al., "Classification of Alpha1-Adrenoceptor Subtypes", Naunyn-Schmiedeberg's Arch Pharmacol., (1995), pp. 1-10, vol. 352.
Reis et al., "The Imidazoline Receptor: Pharmacology, Functions, Ligands, and Relevance to Biology and Medicine", Annals of the New York Academy of Sciences, (1995), vol. 763, Table of Contents.
Yoo et al., "The Conformation and Activity of Benzofuran Derivatives as Angiotensin II Receptor Antagonists", Bioorganic & Medicinal Chemistry, (1997), pp. 445-459, vol. 5. No. 2.
Yoshiya et al., "Synthesis and α-adrenergic Activities of 2- and 4-Substituted Imidazoline and Imidazole Analogues", Journal of Medicinal Chemistry, American Chemical Society, (1992), pp. 750-755, vol. 35, No. 4, XP002151512.
Zhang et al., "Medetomidine Analogs as alpha 2-Adrenergic Ligands. 2. Design, Synthesis and Biological Activity of Conformationally Restricted Naphthalene Derivatives of Medetomidine", Journal of Medicinal Chemistry, American Chemical Society, (1996), pp. 3001-3013, vol. 39.
Written Opinion of the International Searching Authority for PCT/US2008/001808)—AL06621, 9 pages, 2009.
International Search Report (PCT/US2008/001808) for AL06621 mail date Jul. 24, 2008, 6 pages.

*Primary Examiner* — Joseph Kosack
*Assistant Examiner* — Matthew Coughlin
(74) *Attorney, Agent, or Firm* — Gerard Devlin; H. Eric Fischer

(57) ABSTRACT

In its many embodiments, the present invention provides a novel class of naphthene- and indane-type as inhibitors of α2C adrenergic receptor agonists, methods of preparing such compounds, pharmaceutical compositions containing one or more such compounds, methods of preparing pharmaceutical formulations comprising one or more such compounds, and methods of treatment, prevention, inhibition, or amelioration of one or more conditions associated with the α2C adrenergic receptors using such compounds or pharmaceutical compositions.

10 Claims, No Drawings

FUNCTIONALLY SELECTIVE ALPHA2C ADRENORECEPTOR AGONISTS

RELATED APPLICATIONS

This application claims priority to U.S. application Ser. No. 60/901,064, filed on Feb. 13, 2007, herein incorporated by reference.

FIELD OF THE INVENTION

The present invention relates to naphthene- and indane-type compounds useful as α2C adrenergic receptor agonists, methods for making the compounds, pharmaceutical compositions containing the compounds, and methods of treatment and prevention using the compounds and compositions to treat disease states such as congestion (including nasal), migraine, congestive heart failure, cardiac ischemia, glaucoma, stress-induced urinary incontinence, attention deficit hyperactivity disorder, pain and psychotic disorders without substantial adverse side effects associated with α2A receptor agonist treatments.

BACKGROUND OF THE INVENTION

The initial classification of adrenergic receptors into α- and β-families was first described by Ahlquist in 1948 (Ahlquist R P, "A Study of the Adrenergic Receptors," Am. J. Physiol. 153:586-600 (1948)). Functionally, the α-adrenergic receptors were shown to be associated with most of the excitatory functions (vasoconstriction, stimulation of the uterus and pupil dilation). β-adrenergic receptors were implicated in vasodilation, bronchodilation and myocardial stimulation (Lands et al., "Differentiation of Receptor Systems Activated by Sympathomimetic amines," Nature 214:597-598 (1967)). Since this early work, α-adrenergic receptors have been subdivided into α1- and α2-adrenergic receptors. Cloning and expression of α-adrenergic receptors have confirmed the presence of multiple subtypes of both α1 -(α1A, α1B, α1D) and α2-(α2A, α2B, α2C) adrenergic receptors (Michel et al., "Classification of $\alpha_1$-Adrenoceptor Subtypes," Naunyn-Schmiedeberg's Arch. Pharmacol, 352:1-10 (1995); Macdonald et al., "Gene Targeting—Homing in on $\alpha_2$-Adrenoceptor-Subtype Function," TIPS, 18:211-219 (1997)).

Current therapeutic uses of α-2 adrenergic receptor drugs involve the ability of those drugs to mediate many of the physiological actions of the endogenous catecholamines. There are many drugs that act on these receptors to control hypertension, intraocular pressure, eye reddening and nasal congestion and induce analgesia and anesthesia.

α2 adrenergic receptors can be found in the rostral ventrolateral medulla, and are known to respond to the neurotransmitter norepinephrine and the antihypertensive drug clonidine to decrease sympathetic outflow and reduce arterial blood pressure (Bousquet et al., "Role of the Ventral Surface of the Brain Stem in the Hypothesive Action of Clonidine," Eur. J. Pharmacol., 34:151-156 (1975); Bousquet et al., "Imidazoline Receptors: From Basic Concepts to Recent Developments," 26:S1-S6 (1995)). Clonidine and other imidazolines also bind to imidazoline receptors (formerly called imidazoline-guanidinium receptive sites or IGRS) (Bousquet et al., "Imidazoline Receptors: From Basic Concepts to Recent Developments," 26:S1-S6 (1995)). Some researchers have speculated that the central and peripheral effects of imidazolines as hypotensive agents may be related to imidazoline receptors (Bousquet et al., "Imidazoline Receptors: From Basic Concepts to Recent Developments," 26:S1-S6 (1995); Reis et al., "The Imidazoline Receptor: Pharmacology, Functions, Ligands, and Relevance to Biology and Medicine," Ann. N.Y. Acad. Sci., 763:1-703 (1995).

Compounds having adrenergic activity are well-known in the art, and are described in numerous patents and scientific publications It is generally known that adrenergic activity is useful for treating animals of the mammalian species, including humans, for curing or alleviating the symptoms and conditions of numerous diseases and conditions. In other words, it is generally accepted in the art that pharmaceutical compositions having an adrenergic compound or compounds as the active ingredient are useful for treating, among other things, glaucoma, chronic pain, migraines, heart failure, and psychotic disorders.

For example, published PCT application WO 02/076950 discloses compounds having α2 agonist activity of the following general formula:

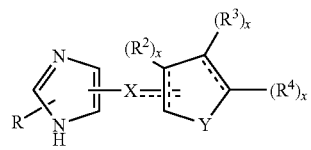

Other publications disclosing similar compounds include WO 01/00586, WO 99/28300, U.S. Pat. No. 6,841,684 B2 and US 2003/0023098 A1.

Another class of compounds having α2-agonist properties is disclosed in U.S. Pat. No. 5,658,938. This class has the following general formula:

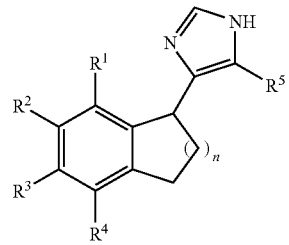

wherein n=1-2, $R^1$-$R^3$ represent hydrogen, halogen hydroxy, alkyl or alkoxy, and $R^5$ is hydrogen or alkyl.

Another class of compounds reported to have affinity for α2 receptors includes the following two compounds (Bagley et.al., Med. Chem. Res. 1994, 4:346-364):

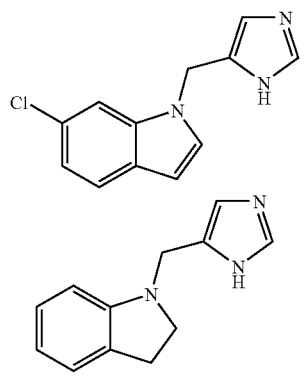

Another class of indane and tetrahyrdonaphthalene type compounds having α2-agonist properties is disclosed in PCT application WO 1997/12874 and WO 2004/0506356 This class has the following general formula:

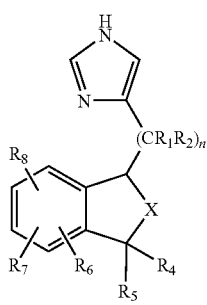

wherein n=0-1, X is 1 or 2 carbon units, $R_4$ is H, OH, alkyl, or alkoxy, $R_5$ may be taken together with $R^4$ to form a carbonyl, and $R^6$-$R^8$=H, OH, SH, alkyl, alkenyl, cycloalkyl, alkoxy, hydroxyalkyl, alkylthio, alkylthiol, halo, $CF_3$, $NO_2$, or alkylamino. This class specifically includes MPV-2426 (fadolmidine) and its prodrug esters:

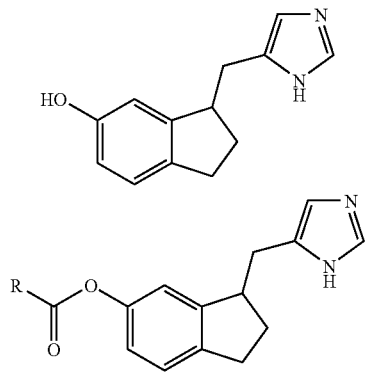

wherein R is optionally substituted lower alkyl, aryl, cycloalkyl, heteroaryl, lower alkylamino, and saturated. 5- or 6-membered heterocyclic groups containing. 1 or 2 N atoms.

It is also known that compounds having adrenergic activity, such as α2A agonists, may be associated with undesirable side effects. Examples of such side effects include hyper- and hypotension, sedation, locomotor activity, and body temperature variations.

Further, other classes of compounds that exhibit functional selectivity for the alpha 2C receptor have been discovered. Application U.S. Ser. No. 11/508,458, filed Aug. 23, 2006, discloses indoline compounds that possess this activity and application U.S. Ser. No. 11/508,467, filed on the same date, describes morpholine compounds that are functionally selective of the alpha 2C receptor. CIP applications of these applications have been filed; the Ser. Nos. are 11/705,673 and 11/705,683, both filed on Feb. 13, 2009.

Additional applications filed concurrently herewith that disclose alpha2C receptor antagonists are application U.S. Ser. No. PCT US08/01765, which claims priority to provisional application U.S. Ser. No. 60/901,045, (AL06619) and application PCT US08/01770, which claims priority to provisional applications U.S. Ser. Nos. 60/901,071 and 60/972,892, (AL06620).

It has been discovered in accordance with the present invention that adrenergic compounds that act selectively, and preferably even specifically, as agonists of the α2C or the α2B/α2C (hereinafter referred to as α2C or α2B/2C) receptor subtypes in preference over the α2A receptor subtype and that act functionally selectively as agonists of the α2C or the α2B/2C receptor subtype in preference over the α2A receptor subtype possess desirable therapeutic properties associated with adrenergic receptors but without having one or more undesirable side effects such as changes in blood pressure or sedation. For the purposes of the present invention, a compound is defined to be a specific or at least functionally selective agonist of the α2C receptor subtype over the α2A receptor subtype if the compound's efficacy at the α2C receptor is ≧30% $E_{max}$ (GTPγS assay) and its efficacy at the α2A receptor is ≦35% $E_{max}$, with an efficacy at the α2A receptor ≦30% $E_{max}$ preferred (GTPγS assay).

There is a need for new compounds, formulations, treatments and therapies to treat diseases and disorders associated with α2C adrenergic receptors while minimizing adverse side effects. Further, there is a need to develop compounds that are functionally selective for the α2C or the α2B/2C receptor subtype with respect to the α2A receptor subtype. It is, therefore, an object of this invention to provide compounds useful in the treatment or prevention or amelioration of such diseases and disorders.

SUMMARY OF THE INVENTION

In its many embodiments, the present invention provides a novel class of heterocyclic compounds as functionally selective α2C adrenergic receptor agonists, or metabolites, stereoisomers, salts, solvates or polymorphs thereof, methods of preparing such compounds, pharmaceutical compositions comprising one or more such compounds, methods of preparing pharmaceutical formulations comprising one or more such compounds, and methods of treatment, prevention, inhibition or amelioration of one or more conditions associated with α2C receptors using such compounds or pharmaceutical compositions.

In one aspect, the present application discloses a compound, or pharmaceutically acceptable salts, esters, prodrugs, metabolites, solvates or polymorphs of said compound, said compound having the general structure shown in Formula I:

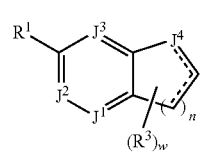

I wherein:
$J^4$ is:

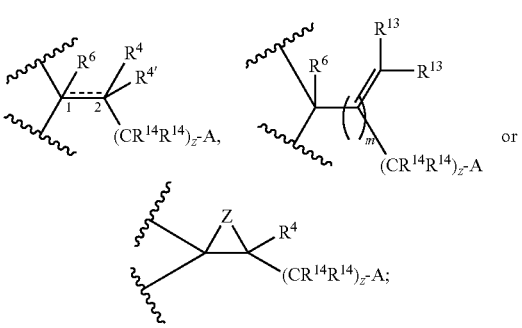

where
Z is —[C($R^c$)($R^c$)]$_x$—, and
x is 1, 2, or 3;

wherein:

A is a 5-membered heteroaryl, heterocyclyl or heterocyclenyl ring containing 1-3 heteroatoms, preferably selected from the group consisting of —O—, —S— and —N—, and is optionally substituted with at least one (preferably 1 to 5, more preferably 1 to 3) $R^5$ and/or 1 or 2 (=O) (carbonyl);

$J^1$, $J^2$, and $J^3$ are independently —N—, —N(O)— or —C($R^2$)—;

----- is a single or double bond provided that there cannot be two continuous double bonds and further provided that when atoms 1 and 2 form a double bond in Formula I, $R^{4'}$ and $R^6$ are not present;

$R^1$ is selected from the group consisting of —[C($R^a$)($R^b$)]$_q$YR$^{7'}$, —[C($R^a$)($R^b$)]$_q$N($R^7$)YR$^{7'}$, —[C($R^a$)($R^b$)]$_q$NR$^7$R$^{7'}$, —[C($R^a$)($R^b$)]$_q$OYR$^{7'}$, —[C($R^a$)($R^b$)]$_q$ON=CR$^7$R$^{7'}$, —P(=O)(OR$^7$)(OR$^{7'}$), —P(=O)(NR$^7$R$^{7'}$)$_2$, and —P(=O)R$^8_2$;

Y is independently selected from the group consisting of a —C(=O)—, —C(=O)NR$^7$—, —C(=O)O—, —C(=O)—[C($R^a$)($R^b$)]$_n$—O—C(=O)—, —C(=O)N(R$^c$)—O—, —C(=NR$^7$)—, —C(=NOR$^7$)—, —C(=NR$^7$)NR$^7$—, —C(=NR$^7$)N(R$^c$)O—, —S(O)$_p$—, —SO$_2$NR$^7$—, and —C(=S)NR$^7$;

wherein $R^a$ and $R^b$ are independently selected from the group consisting of H, alkyl, alkoxy, and halo, and $R^c$ is H or alkyl;

$R^2$ is independently selected from the group consisting of H, —OH, halo, —CN, —NO$_2$, —S(O)$_p$R$^7$, —NR$^7$R$^{7'}$, —(CH$_2$)$_q$YR$^{7'}$, —(CH$_2$)$_q$N(R$^7$)YR$^{7'}$, —(CH$_2$)$_q$OYR$^{7'}$, and —(CH$_2$)$_q$ON=CR$^7$R$^{7'}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$;

$R^3$ is independently selected from the group consisting of H, halo and (=O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$, provided that when w is 3, no more than 2 of the $R^3$ groups may be (=O);

$R^4$ is independently selected from the group consisting of H, —CN, and halo and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$;

$R^{4'}$ is absent or independently selected from the group consisting of H and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$;

$R^5$ is independently selected from the group consisting of H, halo, —OH, —CN, —NO$_2$, —NR$^7$R$^{7'}$, and —S(O)$_p$R$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7$R$^{7'}$, and —S(O)$_p$R$^7$ substituents and/or 1 or 2 (=O);

$R^6$ is absent or independently selected from the group consisting of H, —CN, halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7$R$^{7'}$, and —S(O)$_p$R$^7$ substituents and/or 1 or 2 (=O), and —C(=O)R$^7$, —C(=O)OR$^7$, —C(=O)NR$^7$R$^{7'}$, —SO$_2$R$^7$ and —SO$_2$NR$^7$R$^{7'}$;

$R^7$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times (preferably 1 to 5, more preferably 1 to 3) by $R^{12}$;

$R^{7'}$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times (preferably 1 to 5, more preferably 1 to 3) by $R^{12}$; or a) when a variable is —NR$^7$R$^{7'}$, —[C($R^a$)($R^b$)]$_q$YR$^{7'}$, —[C($R^a$)($R^b$)]$_q$N($R^7$)YR$^{7'}$, —[C($R^a$)($R^b$)]$_q$NR$^7$R$^{7'}$, —[C($R^a$)($R^b$)]$_q$OYR$^{7'}$, —(CH$_2$)$_q$NR$^7$R$^{7'}$, —C(O)NR$^7$R$^{7'}$ or —SO$_2$NR$^7$R$^{7'}$, $R^7$ and $R^{7'}$ together with the nitrogen atom to which they are attached independently form a 3- to 8-membered heterocyclyl, heterocyclenyl or heteroaryl ring having, in addition to the N atom, 1 or 2 additional hetero atoms independently selected from the group consisting of O, N, —N($R^9$)— and S, wherein said rings are optionally substituted by 1 to 5 independently selected $R^5$ moieties and/or 1 or 2 (=O), or b) when a variable is —(CH$_2$)$_q$ON=CR$^7$R$^{7'}$ or —[C($R^a$)($R^b$)]$_q$ON=CR$^7$R$^{7'}$, $R^7$ and $R^{7'}$ together with the carbon atom to which they are attached independently form a 3- to 8-membered cycloalkyl, cycloalkenyl, aryl, heterocyclyl, heterocyclenyl or heteroaryl ring, wherein said hetroacyclyl, heterocyclenyl or heteroaryl rings have 1-3 heteroatoms which are independently selected from the group consisting of O, N, —N($R^9$)— and S, wherein said rings are optionally substituted by 1 to 5 independently selected $R^5$ moieties and/or 1 or 2 (=O);

$R^8$ is independently selected from the group consisting of alkyl, alkenyl, alkynyl, cycloalkyl, aryl, arylalkyl, heterocyclyl, heteroaryl, and heteroarylalkyl groups, each of which is optionally substituted with at least one (preferably 1 to 5, more preferably 1 to 3) of halo, alkoxy, —OH, —CN, —NO$_2$, —N(R$^{11}$)$_2$, and —S(O)$_p$R$^{11}$ substituents and/or 1 or 2 (=O);

$R^9$ is independently selected from the group consisting of H, —C(O)—R$^{10}$, —C(O)—OR$^{10}$, and —S(O)$_p$—OR$^{10}$ and alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO$_2$, —N(R$^{11}$)$_2$, and —S(O)$_p$R$^{11}$ substituents and/or 1 or 2 (=O);

$R^{10}$ is selected from the group consisting of alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO$_2$, —N(R$^{11}$)$_2$, and —S(O)$_p$R$^{11}$ substituents and/or 1 or 2 (=O);

$R^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, each of which is optionally substituted by at least one (preferably 1 to 5, more preferably 1 to 3) substituent independently selected from the group consisting of halo, —OH, —CN, —NO$_2$, —N(R$^{11'}$)$_2$, and —S(O)$_p$R$^{11'}$ substituents and/or 1 or 2 (=O);

$R^{11'}$ is independently selected from the group consisting of H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

$R^{12}$ is independently selected from the group consisting of H, halo, —OH, —CN, —NO$_2$, —N(R$^{11}$)$_2$, and —S(O)$_p$R$^{11}$, and/or 1 or 2 (=O), and alkyl, alkoxy, alkenyl, alkenyloxy, alkynyl, cycloalkyl, cycloalkenyl, cycloalkoxy, aryl, aryloxy, arylalkyl, heteroaryl, heteroaryloxy, heteroarylalkyl, heterocyclyl, heterocyclenyl, heterocyclenyloxy, heterocyclylalkyl, heterocyclenylalkyl, arylalkoxy, heteroarylalkoxy, heterocyclylalkoxy, and heterocyclenylalkoxy groups, each of which in turn is optionally substituted by at least once (preferably 1 to 5, more preferably 1 to 3) by a substituent selected from the group consisting of H, alkyl, haloalkyl, halo, —OH, optionally substituted alkoxy, optionally substituted aryloxy, optionally substituted cycloalkoxy, optionally substituted heteroaryloxy, optionally substituted heterocyclenyloxy, —CN, —NO$_2$, —N(R$^{11}$)$_2$, and —S(O)$_p$R$^{11}$ and/or 1 or 2 (=O), wherein said optionally substituted alkoxy, aryloxy, optionally substituted cycloalkoxy, optionally substituted heteroaryloxy, and heterocyclenyloxy when substituted are substituted one or more (preferably 1 to 5, more preferably 1 to 3) times by $R^{11}$;

$R^{13}$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$;

$R^{14}$ is independently selected from the group consisting of H, alkyl, halo, —CN, and alkoxy;

m is 0 or 1;
n is independently 1, 2, or 3;
p is independently 0, 1, or 2;
q is independently an integer from 0-10;
w is 0, 1, 2, 3, 4, or 5; and
z is 0, 1, 2, 3, 4, or 5,
provided that a) when m is 0, z cannot be 0;

b) if $J^1$-$J^3$ are —C(H)—, $R^1$ is —[C(R$^a$)(R$^b$)]$_q$OYR$^{7'}$, q is 0, and A is unsubstituted imidazolyl, then Y cannot be a bond or —C(=O)—;

c) if $J^1$-$J^3$ are —C(H)—, $R^1$ is —[C(R$^a$)(R$^b$)]$_q$YR$^{7'}$, q is 0, and A is unsubstituted imidazolyl, then Y cannot be a bond, —C(=O)— or —C(=O)O—;

d) if $J^1$-$J^3$ are —C(H)—, $R^1$ is —[C(R$^a$)(R$^b$)]$_q$YR$^{7'}$, q is 0, and A is unsubstituted imidazolyl, and Y is S(O)$_p$—, then p is other than 0;

e) if $J^1$-$J^3$ are —C(H)—, $R^1$ is —[C(R$^a$)(R$^b$)]$_q$YR$^{7'}$, q is ≥1, A is unsubstituted imidazolyl, and Y is a bond, then $R^{7'}$ cannot be H;

f) if $J^1$-$J^3$ are —C(H)—, $R^1$ is —[C(R$^a$)(R$^b$)]$_q$NR$^7$R$^{7'}$, A is unsubstituted imidazolyl, then q is other than zero;

g) if $J^1$-$J^3$ are —C(H)—, $R^1$ is —[C(R$^a$)(R$^b$)]$_q$NR$^7$YR$^{7'}$, A is unsubstituted imidazolyl, q is 0, then Y is other than a bond;

h) if $J^1$-$J^3$ are —C(H)—, $R^1$ is —[C(R$^a$)(R$^b$)]$_q$OYR$^{7'}$, q is ≥1, Y is a bond and A is unsubstituted imidazolyl, then $R^{7'}$ is other than alkyl.

i) if $R^1$ is —[C(R$^a$)(R$^b$)]$_q$YR$^{7'}$, q=0, and Y=—C(=NR$^7$)—, —C(=NOR$^7$)—, —C(=NR$^7$)NR$^7$—, or —C(=NR$^7$)N(R$^c$)O—, then $R^7$ and $R^{7'}$ may not be taken together to form a 3- to 8-membered heterocyclyl, heterocyclenyl or heteroaryl ring; and j) if $R^1$ is —[C(R$^a$)(R$^b$)]$_q$N(R$^7$)YR$^{7'}$ or —[C(R$^a$)(R$^b$)]$_q$NR$^7$R$^{7'}$ and q=0, the $R^7$ and $R^{7'}$ may not be taken together to form a 3- to 8-membered eterocyclyl, heterocyclenyl or heteroaryl ring.

Compounds described in the present application include a compound, or pharmaceutically acceptable salts, esters, prodrugs, metabolites, solvates or polymorphs of said compound, said compound having the general structure shown in Formulae Ia or Ib:

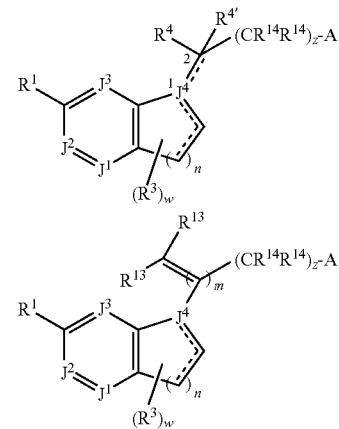

or
Formula Ia Formula Ib
wherein:

A is a 5-membered heteroaryl, heterocyclyl or heterocyclenyl ring containing 1-3 heteroatoms, preferably selected from the group consisting of —O—, —S— and —N—, and is optionally substituted with at least one (preferably 1 to 5, more preferably 1 to 3) $R^5$ and/or 1 or 2 (=O) (carbonyl);

$J^1$, $J^2$, and $J^3$ are independently —N—, —N(O)— or —C(R$^2$)—;

$J^4$ is —C— or —C(R$^6$)—;

----- is a single or double bond provided that there cannot be two continuous double bonds and further provided that when atoms 1 and 2 form a double bond in Formula Ia, $R^{4'}$ and $R^6$ are not present;

$R^1$ is selected from the group consisting of —[C(R$^a$)(R$^b$)]$_q$YR$^{7'}$, —[C(R$^a$)(R$^b$)]$_q$N(R$^7$)YR$^{7'}$, —[C(R$^a$)(R$^b$)]$_q$NR$^7$R$^{7'}$, —[C(R$^a$)(R$^b$)]$_q$OYR$^{7'}$, —[C(R$^a$)(R$^b$)]$_q$ON=CR$^7$R$^{7'}$, —P(=O)(OR$^7$)(OR$^{7'}$), —P(=O)(NR$^7$R$^{7'}$)$_2$, and —P(=O)R$^8_2$;

Y is independently selected from the group consisting of a —C(=O)—, —C(=O)NR$^7$—, —C(=O)O—, —C(=O)—[C(R$^a$)(R$^b$)]$_n$—O—C(=O)—, —C(=O)N(R$^c$)—O—, —C(=NR$^7$)—, —C(=NOR$^7$)—, —C(=NR$^7$)NR$^7$—, —C(=NR$^7$)N(R$^c$)O—, —S(O)$_p$—, —SO$_2$NR$^7$—, and —C(=S)NR$^7$;

wherein $R^a$ and $R^b$ are independently selected from the group consisting of H, alkyl, alkoxy, and halo, and $R^c$ is H or alkyl;

$R^2$ is independently selected from the group consisting of H, —OH, halo, —CN, —NO$_2$, —S(O)$_p$R$^7$, —NR$^7$R$^{7'}$, —(CH$_2$)$_q$YR$^{7'}$, —(CH$_2$)$_q$N(R$^7$)YR$^{7'}$, —(CH$_2$)$_q$OYR$^{7'}$, and —(CH$_2$)$_q$ON=CR$^7$R$^{7'}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$;

$R^3$ is independently selected from the group consisting of H, halo and (=O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$, provided that when w is 3, no more than 2 of the $R^3$ groups may be (=O);

$R^4$ is independently selected from the group consisting of H, —CN, and halo and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$;

$R^{4'}$ is absent or independently selected from the group consisting of H and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$;

$R^5$ is independently selected from the group consisting of H, halo, —OH, —CN, —NO$_2$, —NR$^7$R$^{7'}$, and —S(O)$_p$R$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7$R$^{7'}$, and —S(O)$_p$R$^7$ substituents and/or 1 or 2 (=O);

$R^6$ is absent or independently selected from the group consisting of H, —CN, halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7$R$^{7'}$, and —S(O)$_p$R$^7$ substituents and/or 1 or 2 (=O), and —C(=O)R$^7$, —C(=O)OR$^7$, —C(=O)NR$^7$R$^{7'}$, —SO$_2$R$^7$ and —SO$_2$NR$^7$R$^{7'}$;

or $R^4$ and $R^6$ taken together with the carbon atoms to which they are attached form a 3- to 6-membered cycloalkyl, cycloalkenyl, hetrocyclyl or heterocyclylalkenyl ring, wherein said rings may be optionally substituted one or more times (preferably 1 to 5, more preferably 1 to 3) by $R^5$ and/or 1 or 2 (=O);

$R^7$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times (preferably 1 to 5, more preferably 1 to 3) by $R^{12}$;

$R^{7'}$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times (preferably 1 to 5, more preferably 1 to 3) by $R^{12}$ a) when a variable is —NR$^7$R$^{7'}$, —[C(R$^a$)(R$^b$)]$_q$YR$^{7'}$, —[C(R$^a$)(R$^b$)]$_q$N(R$^7$)YR$^{7'}$, —[C(R$^a$)(R$^b$)]$_q$NR$^7$R$^{7'}$, —[C(R$^a$)(R$^b$)]$_q$OYR$^{7'}$, —(CH$_2$)$_q$NR$^7$R$^{7'}$, —C(O)NR$^7$R$^{7'}$ or —SO$_2$NR$^7$R$^{7'}$, R$^7$ and R$^{7'}$ together with the nitrogen atom to which they are attached independently form a 3- to 8-membered heterocyclyl, heterocyclenyl or heteroaryl ring having, in addition to the N atom, 1 or 2 additional hetero atoms independently selected from the group consisting of O, N, —N(R$^9$)— and S, wherein said rings are optionally substituted by 1 to 5 independently selected R$^5$ moieties and/or 1 or 2 (=O), or b) when a variable is —(CH$_2$)$_q$ON=CR$^7$R$^{7'}$ or —[C(R$^a$)(R$^b$)]$_q$ON=CR$^7$R$^{7'}$, R$^7$ and R$^{7'}$ together with the carbon atom to which they are attached independently form a 3- to 8-membered cycloalkyl, cycloalkenyl, aryl, heterocyclyl, heterocyclenyl or heteroaryl ring, wherein said hetroacyclyl, heterocyclenyl or heteroaryl rings have 1-3 heteroatoms which are independently selected from the group consisting of O, N, —N(R$^9$)— and S, wherein said rings are optionally substituted by 1 to 5 independently selected R$^5$ moieties and/or 1 or 2 (=O);

$R^8$ is independently selected from the group consisting of alkyl, alkenyl, alkynyl, cycloalkyl, aryl, arylalkyl, heterocyclyl, heteroaryl, and heteroarylalkyl groups, each of which is optionally substituted with at least one (preferably 1 to 5, more preferably 1 to 3) of halo, alkoxy, —OH, —CN, —NO$_2$, —N(R$^{11}$)$_2$, and —S(O)$_p$R$^{11}$ substituents and/or 1 or 2 (=O);

$R^9$ is independently selected from the group consisting of H, —C(O)—R$^{10}$, —C(O)—OR$^{10}$, and —S(O)$_p$—OR$^{10}$ and alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO$_2$, —N(R$^{11}$)$_2$, and —S(O)$_p$R$^{11}$ substituents and/or 1 or 2 (=O);

$R^{10}$ is selected from the group consisting of alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO$_2$, —N(R$^{11}$)$_2$, and —S(O)$_p$R$^{11}$ substituents and/or 1 or 2 (=O);

$R^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, each of which is optionally substituted by at least one (preferably 1 to 5, more preferably 1 to 3) substituent independently selected from the group consisting of halo, —OH, —CN, —NO$_2$, —N(R$^{11}$)$_2$, and —S(O)$_p$R$^{11}$ substituents and/or 1 or 2 (=O);

$R^{11'}$ is independently selected from the group consisting of H, alkyl, alkoxy, alkenyl, alkenyloxy, alkynyl, cycloalkyl, cycloalkoxy, aryl, aryloxy, aryloxy, aryloxy, arylalkyl, heteroaryl, heteroarylalkyl, heterocyclyl, and heterocyclylalkyl;

$R^{12}$ is independently selected from the group consisting of H, halo, —OH, —CN, —NO$_2$, —N(R$^{11}$)$_2$, and —S(O)$_p$R$^{11}$, and/or 1 or 2 (=O), and alkyl, alkoxy, alkenyl, alkenyloxy, alkynyl, cycloalkyl, cycloalkenyl, cycloalkoxy, aryl, aryloxy, arylalkyl, heterocyclenyloxy, heterocyclylalkyl, heterocyclenylalkyl, arylalkoxy, heteroarylalkoxy, heterocyclylalkoxy, and heterocyclenylalkoxy groups, each of which in turn is optionally substituted by at least once (preferably 1 to 5, more preferably 1 to 3) by a substituent selected from the group consisting of H, alkyl, haloalkyl, halo, —OH, optionally substituted alkoxy, optionally substituted aryloxy, optionally substituted cycloalkoxy, optionally substituted heteroaryloxy, optionally substituted heterocyclenyloxy, —CN, —NO$_2$, —N(R$^{11}$)$_2$, and —S(O)$_p$R$^{11}$ and/or 1 or 2 (=O), wherein said optionally substituted alkoxy, aryloxy, optionally substituted cycloalkoxy, optionally substituted heteroaryloxy, and heterocyclenyloxy when substituted are substituted one or more (preferably 1 to 5, more preferably 1 to 3) times by R$^{11}$;

$R^{13}$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocycl, and heterocyclylalkyl groups optionally substituted with at least one (preferably 1 to 5, more preferably 1 to 3) R$^5$;

$R^{14}$ is independently selected from the group consisting of H, alkyl, halo, —CN, and alkoxy;

m is 0 or 1;

n is independently an integer from 1-3;

p is independently an integer from 0-2;

q is independently an integer from 0-10;

w is an integer from 1-3; and z is an integer from 0 to 5, provided that a) when m is 0, z cannot be 0;

b) if $J^1$-$J^3$ are —C(H)—, $R^1$ is —[C($R^a$)($R^b$)]$_q$OYR$^{7'}$, q is 0 and A is unsubstituted imidazolyl, then Y cannot be a bond or —C(=O)—;

c) if $J^1$-$J^3$ are —C(H)—, $R^1$ is —[C($R^a$)($R^b$)]$_q$YR$^{7'}$, q is 0, and A is unsubstituted imidazolyl, then Y cannot be a bond, —C(=O)— or —C(=O)O—;

d) if $J^1$-$J^3$ are —C(H)—, $R^1$ is —[C($R^a$)($R^b$)]$_p$YR$^{7'}$, q is 0, and A is unsubstituted imidazolyl, and Y is S(O)$_p$—, then p is other than 0;

e) if $J^1$-$J^3$ are —C(H)—, $R^1$ is —[C($R^a$)($R^b$)]$_q$YR$^{7'}$, q is 1, A is unsubstituted imidazolyl, and Y is a bond, then $R^{7'}$ cannot be H;

f) if $J^1$-$J^3$ are —C(H)—, $R^1$ is —[C($R^a$)($R^b$)]$_q$NR$^7$R$^{7'}$, A is unsubstituted imidazolyl, then q is other than zero;

g) if $J^1$-$J^3$ are —C(H)—, $R^1$ is —[C($R^a$)($R^b$)]$_q$NR$^7$YR$^{7'}$, A is unsubstituted imidazolyl, q is 0, then Y is other than a bond;

h) if $J^1$-$J^3$ are —C(H)—, $R^1$ is —[C($R^a$)($R^b$)]$_q$OYR$^{7'}$, q is ≥1, Y is a bond and A is unsubstituted imidazolyl, then $R^{7'}$ is other than alkyl.

i) if $R^1$ is —[C($R^a$)($R^b$)]$_q$YR$^{7'}$, q=0, and Y=—C(=NR$^7$)—, —C(=NOR$^7$)—, —C(=NR$^7$)NR$^7$—, or —C(=NR$^7$)N($R^c$)O—, then $R^7$ and $R^{7'}$ may not be taken together to form a 3- to 8-membered heterocyclyl, heterocyclenyl or heteroaryl ring; and j) if $R^1$ is —[C($R^a$)($R^b$)]$_q$N($R^7$)YR$^{7'}$ or —[C($R^a$)($R^b$)]$_1$NR$^7$R$^{7'}$ and q=0, then $R^7$ and $R^{7'}$ may not be taken together to form a 3- to 8-membered heterocyclyl, heterocyclenyl or heteroaryl ring.

The compounds of Formula I (including those of Ia and Ib) can be useful as α2C adrenergic receptor agonists, and can be useful in the treatment and prevention of allergic rhinitis, congestion (including, but not limited to nasal congestion), migraine, congestive heart failure, cardiac ischemia, glaucoma, stress-induced urinary incontinence, attention deficit hyperactivity disorder, neuronal damage from ischemia and psychotic disorders. Further, the compounds of Formula I (including those of Ia and Ib) can be useful in the treatment of pain (both chronic and acute), such as pain that is caused by inflammation, neuropathy, arthritis (including osteo and rheumatoid arthritis), diabetes (e.g., diabetes mellitus or diabetes insipidus) or pain of an unknown origin. Examples of neuropathic pain may include but not limited to; diabetic neuropathy, neuralgia of any etiology (e.g. post-herpetic, trigeminal), chemotherapy-induced neuropathy, HIV, lower back pain of neuropathic origin (e.g. sciatica), traumatic peripheral nerve injury of any etiology, central pain (e.g. post-stroke, thalamic, spinal nerve injury). Other pain that can be treated is nociceptive pain and pain that is visceral in origin or pain that is secondary to inflammation or nerve damage in other diseases or diseases of unknown origin. Further, the compounds of Formula I (including those of Ia and Ib) can be useful in the treatment of symptoms of diabetes. Examples of symptoms of diabetes may include but are not limited to: hyperglycemia, hypertriglyceridemia, increased levels of blood insulin and hyperlipidemia.

Alternatively, the present invention provides for a method for the treatment of congestion in a mammal in need thereof which comprises administering to a mammal an effective dose of at least one compound having adrenergic activity wherein said compound is a functionally selective agonist of the α2c receptor.

A further embodiment of the present invention is a method for the treatment of congestion in a mammal in need thereof which comprises administering to a mammal an effective dose of at least one compound having adrenergic activity wherein said compound is a functionally selective agonist of the α2C receptor, wherein the selective agonist of the α2c receptor has an efficacy that is greater than or equal to 30% $E_{max}$ when assayed in the GTPγS assay and its efficacy at the α2A receptor is ≦35% $E_{max}$ (GTPγS assay).

Another embodiment of the present invention is a method for the treatment of congestion in a mammal in need thereof without modifying the blood pressure at therapeutic doses which comprises administering to the mammal an effective dose of at least one compound having adrenergic activity wherein said compound is a selective agonist of the α2C receptor.

DETAILED DESCRIPTION

In an embodiment, the present invention discloses certain heterocyclic compounds which are represented by structural Formula I, or a pharmaceutically acceptable salt or solvate thereof, wherein the various moieties are as described above.

In one embodiment, $J^1$-$J^3$ are —C(H)—, $R^1$ is —[C($R^a$)($R^b$)]$_q$YR$^{7'}$, q is 0, and A is unsubstituted imidazolyl, and Y is other than a bond.

In another embodiment, $J^1$-$J^3$ are —C(H)—, $R^1$ is —[C($R^a$)($R^b$)]$_q$R$^{7'}$, q is 0, and A is unsubstituted imidazolyl, and Y is —C(=O)NR$^7$—.

In another embodiment A is an optionally substituted 5-membered heteroaryl, heterocyclenyl or heterocyclyl ring. Preferred optionally substituted heteroaryl, heterocyclenyl or heterocyclyl 5-membered rings include, for example, imidazole, thiazole, pyrrole, isoxazole, oxazole, isothiazole, pyrazole, imadazoline, imidazol-2-one, imidazol-2-thione, 2-aminoimidazoline, oxazoline, oxazol-2-one, oxazol-2-thione, 2-aminooxazoline, thiazoline, thiazol-2-one, thiazol-2-thione, 2-aminothiazoline, pyrroline, pyrazoline, pyrrolidine, imidazolidine, and pyrazolidine. A more preferred set of 5-membered rings includes: imidazole, imadazoline, imidazol-2-one, imidazol-2-thione, 2-aminoimidazoline, oxazoline, oxazol-2-one, oxazol-2-thione, and 2-aminooxazoline. A most preferred set of 5-membered rings includes imidazole. Optionally substituents include any of the "ring system substituents" identified below.

In another embodiment, $J^1$-$J^3$ are each —C($R^2$)—.

In another embodiment one of $J^1$-$J^3$ is —N— while the other two variables are each —C($R^2$)—.

In another embodiment, $J^1$ is —N—.

In another embodiment, $J^2$ is —N—.

In another embodiment, $J^3$ is —N—.

In another embodiment, $J^2$ and $J^3$ are both —N—.

In another embodiment, $R^1$ is selected from —(CH$_2$)$_q$YR$^{7'}$, —(CH$_2$)$_q$NR$^7$YR$^{7'}$, —(CH$_2$)$_q$N(YR$^7$)(YR$^{7'}$), —(CH$_2$)$_q$NR$^7$R$^{7'}$, —(CH$_2$)$_q$OYR$^{7'}$ or —(CH$_2$)$_q$ON=CR$^7$R$^{7'}$.

In another embodiment, Y is selected from a bond, —C(=O)—, —C(=O)NR$^7$—, —C(=O)O—, —C(=NR$^7$)—, —C(=NOR$^7$)—, —C(=NR$^7$)NR$^7$—, —C(=NR$^7$)NR$^7$O—, —S(O)$_p$—, —SO$_2$NR$^7$—, and —C(=S)NR$^7$—.

In another embodiment, $R^2$ is independently selected from the group consisting of H, —OH, halo, —CN, —NO$_2$, —S(O)$_p$R$^7$, —NR$^7$R$^{7'}$, —(CH$_2$)$_q$YR$^{7'}$, —(CH$_2$)$_q$NR$^7$YR$^{7'}$, —(CH$_2$)$_q$OYR$^{7'}$, and —(CH$_2$)$_q$ON═CR$^7$R$^{7'}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5) $R^5$.

In another embodiment, $R^3$ is independently selected from H, halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5) $R^5$.

In another embodiment, $R^4$ is independently selected from H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5) $R^5$.

In another embodiment, $R^4$ is independently selected from H, —CN, halo and alkyl.

In another embodiment, $R^{4'}$ is independently selected from H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5) $R^5$, and more preferably, H or alkyl.

In another embodiment, $R^5$ is independently selected from H, halo, —OH, —CN, —NO$_2$, —NR$^7$R$^{7'}$, and —S(O)$_p$R$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5) of halo, —OH, —CN, —NO$_2$, —NR$^7$R$^{7'}$, and —S(O)$_p$R$^7$ substituents.

In another embodiment $R^5$ is a (═O) group.

In another embodiment $R^6$ is absent.

In another embodiment $R^6$ is independently selected from the group consisting of H, halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ substituents, and —C(═O)R$^7$, —C(═O)OR$^7$, —C(═O)NR$^7$R$^{7'}$, —SO$_2$R$^7$ and —SO$_2$NR$^7$R$^{7'}$.

In another embodiment $R^6$ is independently selected from the group consisting of H, —CN, halo, alkyl and —C(═O)R$^7$, —C(═O)OR$^7$, —C(═O)NR$^7$R$^{7'}$, —SO$_2$R$^7$ and —SO$_2$NR$^7$R$^{7'}$.

In another embodiment, when m is 1, $R^4$ and $R^6$ taken together with the carbon atoms to which they are attached form a 3- to 6-membered cycloalkyl, cycloalkenyl, hetrocyclyl or heterocyclylalkenyl ring, wherein said rings may be optionally substituted one or more times (preferably 1 to 5) by $R^5$.

In another embodiment, $R^7$ or $R^{7'}$ is independently selected from H and alkyl, alkenyl, alkynyl, cycloalkyl, aryl, arylalkyl, heterocyclyl, heteroaryl, and heteroarylalkyl groups, each of which is optionally substituted with at least one of halo, alkoxy, —OH, —CN, —NO$_2$, —N(R$^{11}$)$_2$, and —S(O)$_p$R$^{11}$ substituents.

In another embodiment, when a variable is —NR$^7$R$^{7'}$, —[C(R$^a$)(R$^b$)]$_q$YR$^{7'}$, —[C(R$^a$)(R$^b$)]$_q$N(R$^7$)YR$^{7'}$, —[C(R$^a$)(R$^b$)]$_q$NR$^7$R$^{7'}$, —[C(R$^a$)(R$^b$)]$_q$OYR$^{7'}$, —(CH$_2$)$_q$NR$^7$R$^{7'}$, —P(O)NR$^7$R$^{7'}$, —C(O)NR$^7$R$^{7'}$ or —SO$_2$NR$^7$R$^{7'}$, R$^7$ and R$^{7'}$ together with the N atom to which they are attached form a aziridine, azetidine, pyrrole, pyrrolidine, piperidine, piperazine or morpholine ring, each of which are optionally substituted by $R^5$.

In another embodiment, $R^8$ is independently selected from alkyl, alkenyl, alkynyl, cycloalkyl, aryl, arylalkyl, heterocyclyl, heteroaryl, and heteroarylalkyl groups, each of which is optionally substituted with at least one (preferably 1 to 5) of halo, alkoxy, —OH, —CN, —NO$_2$, —N(R$^{11}$)$_2$, and —S(O)$_p$R$^{11}$ substituents.

In another embodiment, $R^{12}$ is independently selected from alkyl, haloalkyl, nitro, cyano, halo, hydroxyl, amino, alkylamino, dialkylamino and alkoxy.

In another embodiment $R^{13}$ is independently H or alkyl.

In another embodiment $R^{14}$ is independently H, alkyl or halo.

In another embodiment A is unsubstituted imidazole, $J^1$-$J^2$ are —C(H)—, $J^3$ is —N— or —C(H)—, $J^4$ is —C— or —C(R$^6$)—, $R^3$ is H, $R^4$ is H, halo or alkyl, $R^6$ is H, n is 1 or 2, and z is 0.

In another embodiment A is unsubstituted imidazole, $J^1$-$J^2$ are —C(H)—, $J^3$ is —N— or —C(H)—, $R^3$ is H, $R^4$ is H, halo or alkyl, $R^6$ is H, $R^{14}$ is H, alkyl or halo, n is 1 or 2, and z is 1-3.

In another embodiment A is unsubstituted imidazole, $J^1$-$J^2$ are —C(H)—, $J^3$ is —N— or —C(H)—, $R^3$ is H, $R^6$ is H, $R^{13}$ is H or alkyl, m is 1, n is 1 or 2, and z is 0.

In another embodiment A is unsubstituted imidazole, $J^1$-$J^2$ are —C(H)—, $J^3$ is —N— or —C(H)—, $J^4$ is —C— or —C(R$^6$)—, $R^3$ is H, $R^6$ is H, $R^{13}$ is H or alkyl, $R^{14}$ is H, alkyl or halo, m is 1, n is 1 or 2, and z is 1-3.

In another embodiment, in Formula I, $R^{4'}$ and $R^5$ are not present and atoms 1 and 2 form a double bond with a trans or cis configuration relative to —(CR$^{14}$R$^{14}$)$_z$-A and the bicyclic ring.

In another embodiment, m is 1 and z is an integer from 0 to 3.

In another embodiment, m is 0 and z is 1 to 5, preferably 1 or 2, most preferably 1.

In another embodiment, n is 1.

In another embodiment, n is 2.

In another embodiment, p is an integer from 0-2.

In another embodiment, q is is an integer from 0-3.

In another embodiment, A is imidazolyl.

In another embodiment, the present invention discloses compound of Formula Ia or Ib

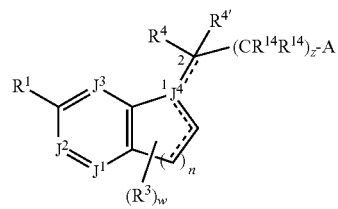

Formula Ia or

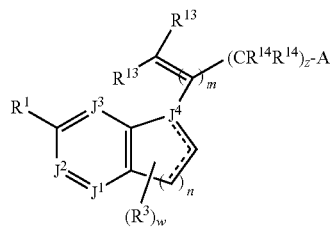

Formula Ib wherein:

A is a 5-membered heteroaryl, heterocyclyl or heterocyclenyl ring containing 1-3 heteroatoms, preferably selected from the group consisting of —O—, —S— and —N—, and is optionally substituted with at least one (preferably 1 to 5, more preferably 1 to 3) $R^5$ and/or 1 or 2 (=O) (carbonyl);

$J^1$, $J^2$, and $J^3$ are independently —N—, —N(O)— or —C($R^2$)—;

$J^4$ is —C— or —C($R^6$)—;

----- is a single or double bond provided that there cannot be two continuous double bonds and further provided that when atoms 1 and 2 form a double bond, $R^{4'}$ is not present;

$R^1$ is selected from the group consisting of —[C($R^a$)($R^b$)]$_q$YR$^{7'}$, —[C($R^a$)($R^b$)]$_q$N($R^7$)YR$^{7'}$, —[C($R^a$)($R^b$)]$_q$NR$^7$R$^{7'}$, —[C($R^a$)($R^b$)]$_q$OYR$^{7'}$, —[C($R^a$)($R^b$)]$_q$ON=CR$^7$R$^{7'}$, —P(=O)(OR$^7$)(OR$^{7'}$), —P(=O)(NR$^7$R$^{7'}$)$_2$, and —P(=O)R$^8_2$;

Y is independently selected from the group consisting of a —C(=O)—, —C(=O)NR$^7$—, —C(=O)O—, —C(=O)—[C($R^a$)($R^b$)]$_n$—O—C(=O)—, —C(=O)N(R$^c$)—O—, —C(=NR$^7$)—, —C(=NOR$^7$)—, —C(=NR$^7$)NR$^7$—, —C(=NR$^7$)N(R$^c$)O—, —S(O)$_p$—, —SO$_2$NR$^7$—, and —C(=S)NR$^7$;

wherein $R^a$ and $R^b$ are independently selected from the group consisting of H, alkyl, alkoxy, and halo, and $R^c$ is H or alkyl;

$R^2$ is selected from the group consisting of H, —OH, halo, —CN, —NO$_2$, —S(O)$_p$R$^7$, —NR$^7$R$^{7'}$, —(CH$_2$)$_q$YR$^{7'}$, —(CH$_2$)$_q$N(R$^7$)YR$^{7'}$, —(CH$_2$)$_q$OYR$^{7'}$, and —(CH$_2$)$_q$ON=CR$^7$R$^{7'}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$;

$R^3$ is independently selected from the group consisting of H, halo and (=O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$, provided that when w is 3, no more than 2 of the $R^3$ groups may be (=O);

$R^4$ is independently selected from the group consisting of H, —CN, and halo and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$;

$R^{4'}$ is absent or independently selected from the group consisting of H and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$;

$R^5$ is independently selected from the group consisting of H, halo, —OH, —CN, —NO$_2$, —NR$^7$R$^{7'}$, and —S(O)$_p$R$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7$R$^{7'}$, and —S(O)$_p$R$^7$ substituents and/or 1 or 2 (=O);

$R^6$ is absent or independently selected from the group consisting of H, —CN and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7$R$^{7'}$, and —S(O)$_p$R$^7$ substituents and/or 1 or 2 (=O), and —C(=O)R$^7$, —C(=O)OR$^7$, —C(=O)NR$^7$R$^{7'}$, —SO$_2$R$^7$ and —SO$_2$NR$^7$R$^{7'}$;

$R^7$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times (preferably 1 to 5, more preferably 1 to 3) by $R^{12}$;

$R^{7'}$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, heterocyclenyl, heterocyclenylalkyl, heteroaryl, and heteroarylalkyl groups, each of which is optionally substituted one or more times (preferably 1 to 5, more preferably 1 to 3) by $R^{12}$ a) when a variable is —NR$^7$R$^{7'}$, —[C($R^a$)($R^b$)]$_q$YR$^{7'}$, —[C($R^a$)($R^b$)]$_q$N(R$^7$)YR$^{7'}$, —[C($R^a$)($R^b$)]$_q$NR$^7$R$^{7'}$, —[C($R^a$)($R^b$)]$_q$OYR$^{7'}$, —(CH$_2$)$_q$NR$^7$R$^{7'}$, —C(O)NR$^7$R$^{7'}$ or —SO$_2$NR$^7$R$^{7'}$, $R^7$ and $R^{7'}$ together with the nitrogen atom to which they are attached independently form a 3- to 8-membered heterocyclyl, heterocyclenyl or heteroaryl ring having, in addition to the N atom, 1 or 2 additional hetero atoms independently selected from the group consisting of O, N, —N(R$^9$)— and S, wherein said rings are optionally substituted by 1 to 5 independently selected $R^5$ moieties and/or 1 or 2 (=O), or b) when a variable is —(CH$_2$)$_q$ON=CR$^7$R$^{7'}$ or —[C($R^a$)($R^b$)]$_q$ON=CR$^7$R$^{7'}$, $R^7$ and $R^{7'}$ together with the carbon atom to which they are attached independently form a 3- to 8-membered cycloalkyl, cycloalkenyl, aryl, heterocyclyl, heterocyclenyl or heteroaryl ring, wherein said hetroacyclyl, heterocyclenyl or heteroaryl rings have 1-3 heteroatoms which are independently selected from the group consisting of O, N, —N(R$^9$)— and S, wherein said rings are optionally substituted by 1 to 5 independently selected $R^5$ moieties and/or 1 or 2 (=O);

$R^8$ is independently selected from the group consisting of alkyl, alkenyl, alkynyl, cycloalkyl, aryl, arylalkyl, heterocyclyl, heteroaryl, and heteroarylalkyl groups, each of which is optionally substituted with at least one (preferably 1 to 5, more preferably 1 to 3) of halo, alkoxy, —OH, —CN, —NO$_2$, —N(R$^{11}$)$_2$, and —S(O)$_p$R$^{11}$ substituents and/or 1 or 2 (=O);

$R^9$ is independently selected from the group consisting of H, 13 C(O)—R$^{10}$, —C(O)—OR$^{10}$, and —S(O)$_p$—OR$^{10}$ and alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO$_2$, —N(R$^{11}$)$_2$, and —S(O)$_p$R$^{11}$ substituents and/or 1 or 2 (=O);

$R^{10}$ is selected from the group consisting of alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO$_2$, —N(R$^{11}$)$_2$, and —S(O)$_p$R$^{11}$ substituents and/or 1 or 2 (=O);

$R^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, each of which is optionally substituted by at least one (preferably 1 to 5, more preferably 1 to 3) substituent independently selected from the group consisting of halo, —OH, —CN, —NO$_2$, —N(R$^{11'}$)$_2$, and —S(O)$_p$R$^{11}$ substituents and/or 1 or 2 (=O);

$R^{11'}$ is independently selected from the group consisting of H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

R[12] is independently selected from the group consisting of H, halo, —OH, —CN, —NO$_2$, —N(R[11])$_2$, and —S(O)$_p$R[11], and/or 1 or 2 (=O), and alkyl, alkoxy, alkenyl, alkenyloxy, alkynyl, cycloalkyl, cycloalkenyl, cycloalkoxy, aryl, aryloxy, arylalkyl, heteroaryl, heteroaryloxy, heteroarylalkyl, heterocyclyl, heterocyclenyl, heterocyclenyloxy, heterocyclylalkyl, heterocyclenylalkyl, arylalkoxy, heteroarylalkoxy, heterocyclylalkoxy, and heterocyclenylalkoxy groups, each of which in turn is optionally substituted by at least once (preferably 1 to 5, more preferably 1 to 3) by a substituent selected from the group consisting of H, alkyl, haloalkyl, halo, —OH, optionally substituted alkoxy, optionally substituted aryloxy, optionally substituted cycloalkoxy, optionally substituted heteroaryloxy, optionally substituted heterocyclenyloxy, —CN, —NO$_2$, —N(R[11])$_2$, and —S(O)$_p$R[11] and/or 1 or 2 (=O), wherein said optionally substituted alkoxy, aryloxy, optionally substituted cycloalkoxy, optionally substituted heteroaryloxy, and heterocyclenyloxy when substituted are substituted one or more (preferably 1 to 5, more preferably 1 to 3) times by R[11];

R[13] is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) R[5];

R[14] is independently selected from the group consisting of H, alkyl, halo, —CN, and alkoxy;

m is 0 or 1;
n is independently 1, 2, or 3;
p is independently 0, 1, or 2;
q is independently an integer from 0-10;
w is 0, 1, 2, or 3; and
z is 0, 1, 2, 3, 4 or 5,
provided that
 a) when m is 0, z cannot be 0;
 b) if J$^1$-J$^3$ are —C(H)—, R$^1$ is —[C(R$^a$)(R$^b$)]$_q$OYR$^{7'}$, q is 0, and A is unsubstituted imidazolyl, then Y cannot be a bond or —C(=O)—;
 c) if J$^1$-J$^3$ are —C(H)—, R$^1$ is —[C(R$^a$)(R$^b$)]$_q$YR$^{7'}$, q is 0, and A is unsubstituted imidazolyl, then Y cannot be a bond, —C(=O)— or —C(=O)O—;
 d) if J$^1$-J$^3$ are —C(H)—, R$^1$ is —[C(R$^a$)(R$^b$)]$_q$YR$^{7'}$, q is 0, and A is unsubstituted imidazolyl, and Y is S(O)$_p$—, then p is other than 0;
 e) if J$^1$-J$^3$ are —C(H)—, R$^1$ is —[C(R$^a$)(R$^b$)]$_q$YR$^{7'}$, q is 1, A is unsubstituted imidazolyl, and Y is a bond, then R$^{7'}$ cannot be H;
 f) if J$^1$-J$^3$ are —C(H)—, R$^1$ is —[C(R$^a$)(R$^b$)]$_q$NR$^7$R$^{7'}$, A is unsubstituted imidazolyl, then q is other than zero;
 g) if J$^1$-J$^3$ are 13 C(H)—, R$^1$ is —[C(R$^a$)(R$^b$)]$_q$NR$^7$YR$^{7'}$, A is unsubstituted imidazolyl, q is 0, then Y is other than a bond;
 h) if J$^1$-J$^3$ are —C(H)—, R$^1$ is —[C(R$^a$)(R$^b$)]$_q$OYR$^{7'}$, q is 1, Y is a bond and A is unsubstituted imidazolyl, then R$^{7'}$ is other than alkyl.
 i) if R$^1$ is —[C(R$^a$)(R$^b$)]$_q$YR$^{7'}$, q=0, and Y=—C(=NR$^7$)—, —C(=NOR$^7$)—, —C(=NR$^7$)NR$^7$—, or —C(=NR$^7$)N(R$^c$)O—, then R$^7$ and R$^{7'}$ may not be taken together to form a 3- to 8-membered heterocyclyl, heterocyclenyl or heteroaryl ring; and
 j) if R$^1$ is —[C(R$^a$)(R$^b$)]$_q$N(R$^7$)YR$^{7'}$ or —[C(R$^a$)(R$^b$)]$_q$NR$^7$R$^{7'}$ and q=0, then R$^7$ and R$^{7'}$ may not be taken together to form a 3- to 8-membered heterocyclyl, heterocyclenyl or heteroaryl ring.

In another embodiment, the present invention discloses compounds which are represented by structural formulae Ia-1 to Ib-6, depicted below, or a pharmaceutically acceptable salt, solvate or ester thereof, wherein the various moieties are as described above:

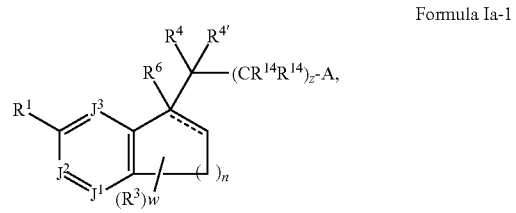

Formula Ia-1

Formula Ia-2

Formula Ib-1

Formula Ib-2

Formula Ib-3

Formula Ib-4

Formula Ib-5 and

Formula Ib-6 wherein n is 1, 2, or 3 and the individual variables, when present are:

$J^1$-$J^2$ are each —C($R^2$)—;

$J^3$ is —C($R^2$)— or —N—;

A is ($R^5$)$_{z'}$-imidazolyl;

$R^1$ is selected from the group consisting of —(CH$_2$)$_q$Y$R^{7'}$ —(CH$_2$)$_q$N($R^7$)Y$R^{7'}$, —(CH$_2$)$_q$N(Y$R^7$)(Y$R^{7'}$), —(CH$_2$)$_q$N$R^7$$R^{7'}$, —(CH$_2$)$_q$OY$R^{7'}$, —(CH$_2$)$_q$ON=C$R^7$$R^{7'}$, —P(=O)(O$R^7$)(O$R^{7'}$), —P(=O)(N$R^7$$R^{7'}$)$_2$, and —P(=O)$R^8{}_2$;

Y is independently selected from the group consisting of a bond, —C(=O)—, —C(=O)N$R^7$—, —C(=O)O—, —C(=N$R^7$)—, —C(=NO$R^7$)—, —C(=N$R^7$)N$R^{7'}$—, —C(=N$R^7$)N$R^7$O—, —S(O)$_p$—, —SO$_2$N$R^7$—, and —C(=S)N$R^7$—;

$R^2$ is independently selected from the group consisting of H, —OH, halo, —CN, —NO$_2$, —S(O)$_p$$R^7$, —N$R^7$$R^{7'}$, —(CH$_2$)$_q$Y$R^{7'}$, —(CH$_2$)$_q$N($R^7$)Y$R^{7'}$, —(CH$_2$)$_q$OY$R^{7'}$, and —(CH$_2$)$_q$ON=C$R^7$$R^{7'}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

$R^3$ is independently selected from the group consisting of H and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

$R^4$ is independently selected from the group consisting of H, —CN, and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

$R^{4'}$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

$R^5$ is independently selected from the group consisting of H, halo, —OH, —CN, —NO$_2$, —N$R^7$$R^{7'}$, and —S(O)$_p$$R^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —N$R^7$$R^{7'}$, and —S(O)$_p$$R^7$ substituents;

$R^6$ is independently selected from the group consisting of H, —CN and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —N$R^7$$R^{7'}$, and —S(O)$_p$$R^7$ substituents, and —C(=O)$R^7$, —C(=O)O$R^7$, —C(=O)N$R^7$$R^{7'}$, —SO$_2$$R^7$ and —SO$_2$N$R^7$$R^{7'}$;

$R^7$ is independently selected from the group consisting of H and alkyl, alkenyl, alkynyl, cycloalkyl, cycloalkylalkyl, cyclocyclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times by $R^{12}$;

$R^{7'}$ is independently selected from the group consisting of H and alkyl, alkenyl, alkynyl, cycloalkyl, cycloalkylalkyl, cyclocyclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times by $R^{12}$; or a) when a variable is —N$R^7$$R^{7'}$, —(CH$_2$)$_q$N$R^7$$R^{7'}$, —P(O)N$R^7$$R^{7'}$, —C(O)N$R^7$$R^{7'}$ or —SO$_2$N$R^7$$R^{7'}$, $R^7$ and $R^{7'}$ together with the nitrogen atom to which they are attached form a 3- to 8-membered heterocyclyl, heterocyclenyl or heteroaryl ring having, in addition to the N atom, 1 or 2 additional hetero atoms selected from the group consisting of O, N, —N($R^9$)— and S, wherein said rings are optionally substituted by 1 to 5 independently selected $R^5$ moieties, $R^8$ is independently selected from the group consisting of alkyl, alkenyl, alkynyl, cycloalkyl, aryl, arylalkyl, heterocyclyl, heteroaryl, and heteroarylalkyl groups, each of which is optionally substituted with at least one of halo, alkoxy, —OH, —CN, —NO$_2$, —N($R^{11}$)$_2$, and —S(O)$_p$$R^{11}$ substituents;

$R^9$ is independently selected from the group consisting of H, —C(O)—$R^{10}$, —C(O)—$R^{10}$, and —S(O)$_p$—O$R^{10}$ and alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N($R^{11}$)$_2$, and —S(O)$_p$$R^{11}$ substituents; and $R^{10}$ is selected from the group consisting of alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N($R^{11}$)$_2$, and —S(O)$_p$$R^{11}$ substituents;

$R^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, each of which is optionally substituted by at least one substituent independently selected from the group consisting of halo, —OH, —CN, —NO$_2$, —N($R^{11}$)$_2$, and —S(O)$_p$$R^{11'}$;

$R^{11'}$ is independently selected from the group consisting of H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

$R^{12}$ is independently selected from selected from the group consisting of H, halo, —OH, —CN, —NO$_2$, —N($R^{11}$)$_2$, and —S(O)$_p$$R^{11}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which in turn is optionally substituted at least once by a substituent selected from the group consisting of alkyl, haloalkyl, halo, —OH, optionally substituted alkoxy, —CN, —NO$_2$, —N($R^{11}$)$_2$, and —S(O)$_p$$R^{11}$, wherein said optionally substituted alkoxy when substituted is substituted one or more times by $R^{11}$;

$R^{13}$ is independently H or alkyl;

$R^{14}$ is independently H or alkyl;

z is 1, 2, 3, 4, or 5;

p is independently 0, 1, or 2;

q is independently an integer from 0-6;

z' is 0, 1, 2 or 3; and w is 0, 1, 2, or 3 or a pharmaceutically acceptable salt, ester, solvate or prodrug thereof.

Preferred compounds of formulae Ia-1 to Ib-6 are those wherein:

$J^1$, $J^2$ and $J^3$ are —(C$R^2$)—;

$R^1$ is —[C($R^a$)($R^b$)]$_q$Y$R^{7'}$ or —[C($R^a$)($R^b$)]$_q$N($R^7$)Y$R^{7'}$;

Y is a —C(=O)—, —C(=O)O—, or —C(=O)N$R^7$;

n is 1, 2 or 3;

$R^6$ is H or alkyl;

$R^7$ is H or optionally substituted alkyl (preferably $C_1$-$C_5$-alkyl);

$R^{7'}$ is optionally substituted alkyl (preferably $C_1$-$C_5$-alkyl), amino, alkylamino, or dialkylamino, p is 0, 1 or 2;

z is 1-3.

Preferred optional substituents include halo, —CN, —NO$_2$, alkoxy, amino, alkylamino, dialkylamino, or optionally substituted phenyl, wherein the substituents on the phenyl moiety are the "ring system substituents" defined below.

In another embodiment, the present invention discloses compounds of formulae Ia-1 or Ib-1 wherein:
$J^1$, $J^2$ and $J^3$ are CH;
$R^1$ is —$(CH_2)_p YR^7$ or —$(CH_2)_q N(R^7)YR^{7'}$;
Y is a —C(=O)—, —C(=O)O—, —S(O)_p—, or —SO_2NR^7—; and, when present,
$R^{4'}$ is H or alkyl,
or a pharmaceutically acceptable salt, ester, solvate or prodrug thereof.

In another embodiment, the present invention discloses compound represented by Formulae II-V or their pharmaceutically acceptable salts, esters, solvates or prodrugs thereof:

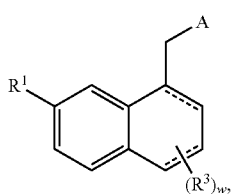

Formula II

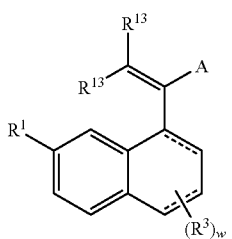

Formula III

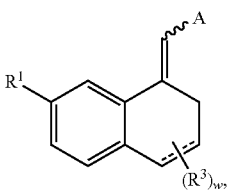

Formula IV

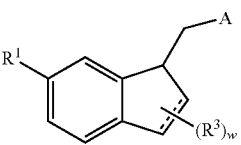

Formula V wherein the individual variables are defined in Formula I above and "∿∿∿" indicates a cis or trans double bond configuration between ring A and the bicyclic ring.

Preferred compounds of Formulae II-V are those wherein
A is imidazole;
$R^1$ is —$[C(R^a)(R^b)]_q YR^{7'}$ or —$[C(R^a)(R^b)]_q N(R^7)YR^{7'}$;
Y is a —C(=O)—, —C(=O)O—, or —C(=O)NR^7—;
q is 0, 1, or 2;
$R^6$ is H or alkyl;
$R^7$ is H or optionally substituted alkyl (preferably $C_1$-$C_5$-alkyl);
$R^{7'}$ is optionally substituted alkyl (preferably $C_1$-$C_5$-alkyl), amino, alkylamino, or dialkylamino, benzyl, wherein the phenyl ring is optionally substituted, and optionally substituted phenyl; the optional substituents are independently alkyl, cyano, halo, nitro, amino, alkylamino and dialkylamino;
q is 0 or 1
p is 0, 1 or 2;
w is 0, 1, or 2;
or a pharmaceutically acceptable salt, ester, solvate or prodrug thereof.

In another embodiment, the present invention discloses compound represented by Formula VI or their pharmaceutically acceptable salts, esters, solvates or prodrugs thereof

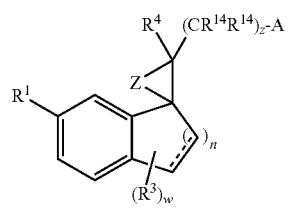

Formula VI wherein the groups, when present, are those describe for Formula I.

A group of compounds is shown below:

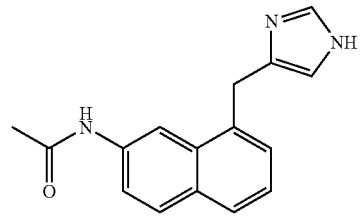

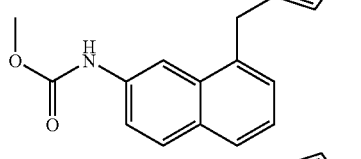

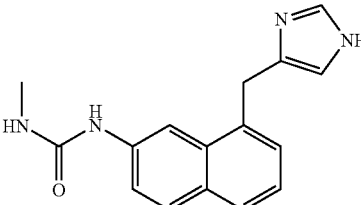

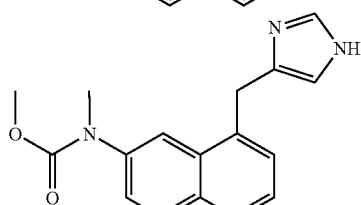

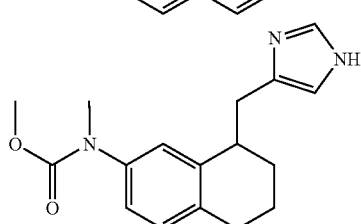

An especially preferred group of compounds is shown below:
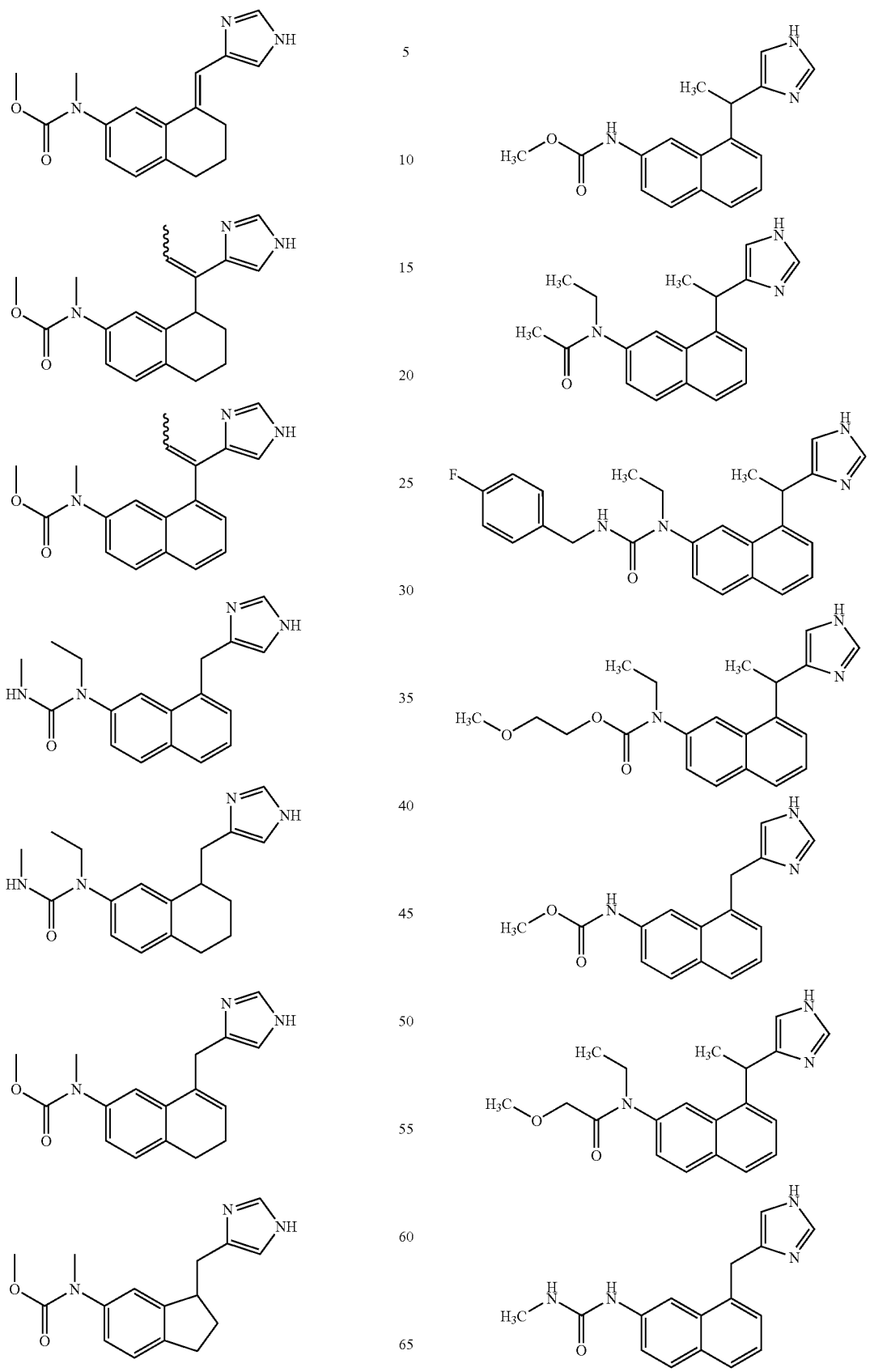

-continued

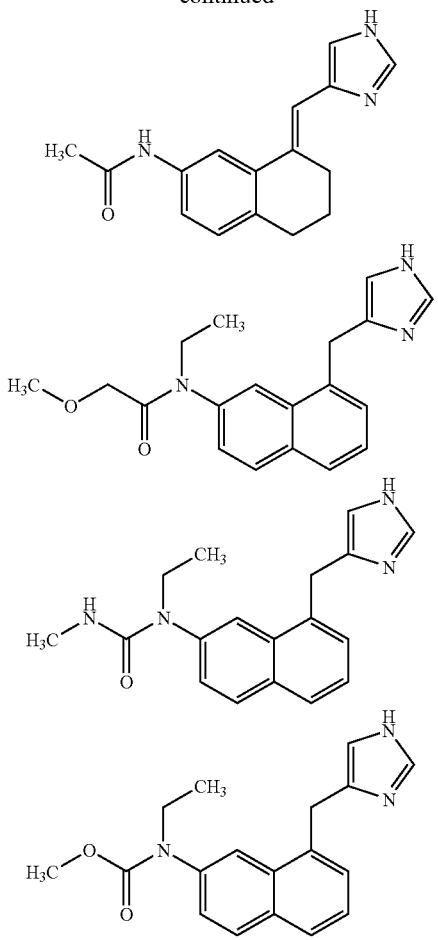

In another embodiment this invention describes a compound of Formula 1 in isolated and purified form In another embodiment this invention describes a method for selectively stimulating α2C adrenergic receptors in a cell in need thereof, comprising contacting said cell with a therapeutically effective amount of at least one compound of Formula I or a pharmaceutically acceptable salt of solvate thereof.

As used above, and throughout this disclosure, the following terms, unless otherwise indicated, shall be understood to have the following meanings:

"Patient" includes both human and animals.

"Mammal" means humans and other mammalian animals.

"Congestion" refers to all type of congestion including, but not limited to, congestion associated with perennial allergic rhinitis, seasonal allergic rhinitis, non-allergic rhinitis, vasomotor rhinitis, rhinitis medicamentosa, sinusitis, acute rhinosinusitis, or chronic rhinosinusitis or when the congestion is caused by polyps or is associated with the common cold.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)₂, carboxy and —C(O)O-alkyl. Non-limiting examples of suitable alkyl groups include methyl, ethyl, n-propyl, isopropyl and t-butyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system, in which at least one of the multicyclic rings is an aryl ring, comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. Non-limiting examples of aryl multicyclic ring systems include:

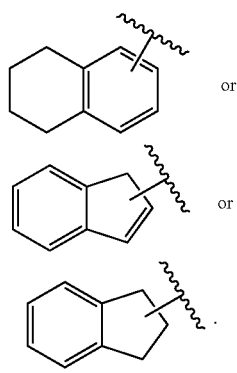

"Heteroaryl" means an aromatic monocyclic or multicyclic ring system, in which at least one of the multicyclic rings is aromatic, comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

Non-limiting examples of heteroaryl multicyclic ring systems systems include:

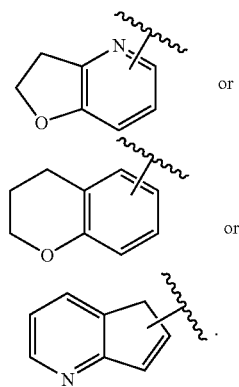

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halogen" and "Halo" mean fluorine, chlorine, bromine, or iodine. Preferred are fluorine, chlorine or bromine, and more preferred are fluorine and chlorine.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, heteroaralkyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different and are independently selected from the group consisting of hydrogen, alkyl, aryl, and aralkyl.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protected moieties are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, imidazolidinyl, pyrazolidinyl, tetrahydrofuranyl, and the like.

Compounds of Formula I, and salts, esters, solvates and prodrugs thereof, may exist in their tautomeric form (for example, as an amide or imino ether). All such tautomeric forms are contemplated herein as part of the present invention. Non-limiting examples of tautomeric forms that are part of this invention are as follows:

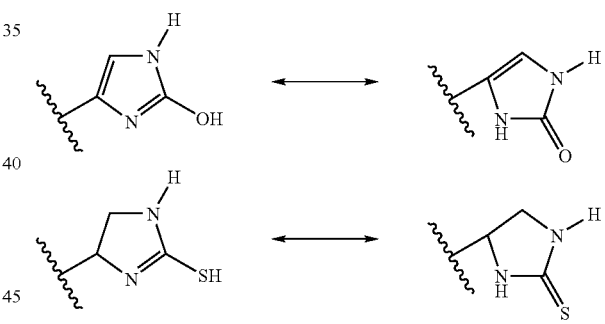

It should be noted that in saturated heterocyclyl containing systems of this invention, there are no hydroxyl, amino, or thiol groups on carbon atoms adjacent to a N, O or S atom. Thus, for example, in the ring:

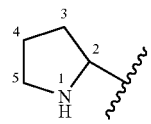

there is no —OH attached directly to carbons marked 2 and 5. It should also be noted that this definition does not preclude (=O), (=S), or (=N) substitutions, or their tautomeric forms, on C atoms adjacent to a N, O or S. Thus, for example, in the above ring, (=O) substitution on carbon 5, or its imino ether tautomer is allowed. Non-limiting examples which illustrate the present invention are as follows:

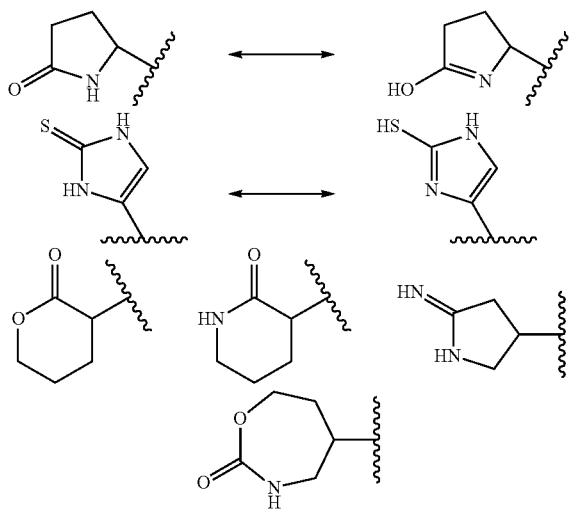

The following non-limiting examples serve to illustrate radicals not contemplated by the present invention:

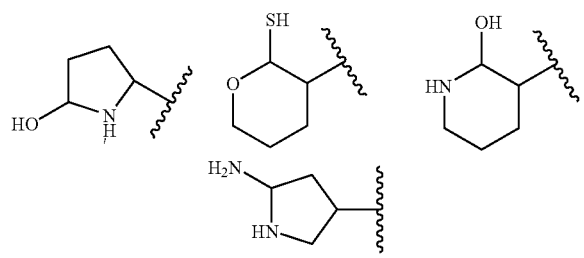

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" or "heteroarylalkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Heterocyclylalkyl" means a heterocyclyl-alkyl group in which the heterocyclyl and the alkyl are as previously described. Preferred heterocyclylalkyls contain a lower alkyl group. Non-limiting examples of suitable heterocyclylalkyl groups include piperidylmethyl, piperidylethyl, pyrrolidylmethyl, morpholinylpropyl, piperazinylethyl, azindylmethyl, azetidylethyl, oxiranylpropyl and the like. The bond to the parent moiety is through the alkyl group.

"Heterocyclenyl" (or "heterocycloalkeneyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4- tetrahydropyridyl, 1,2-dihydropyridyl, 1,4-dihydropyridyl, 1,2,3,6-tetrahydropyridyl, 1,4,5,6-tetrahydropyrimidyl, 2-pyrrolinyl, 3-pyrrolinyl, 2-imidazolinyl, 2-pyrazolinyl, 2-oxazolinyl, 2-thiazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclenylalkyl" means a heterocyclenyl-alkyl group in which the heterocyclenyl and the alkyl are as previously described.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an organic acid group in which the —OH of the carboxyl group is replaced by some other substituent. Suitable non-limiting examples include H—C(O)—, alkyl-C(O)—, cycloalkyl-C(O)—, heterocyclyl-C(O)—, and heteroaryl-C(O)— groups in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" or "arylalkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Heteroarylalkoxy" means a heteroarylalkyl-O-group in which the heteroarylalkyl group is as previously described.

"Heterocyclylalkoxy" means a heterocyclylalkyl-O group in which the hetrocyclylalkyl group is as previously described.

"Heterocyclenylalkoxy" means a heterocyclenylalkyl-O group in which the heterocyclenylalkyl group is as previously described.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

It is noted that carbons of Formula I can be replaced with 1-3 silicon atoms, provided all valency requirements are satisfied.

The term "optionally substituted" means optional substitution with the specified groups, radicals or moieties.

The term "continuous double bonds" means two adjacent double bonds; i.e., —C═C═C—.

The straight line ___ as a bond generally indicates a mixture of, or either of, the possible isomers, non-limiting example(s) include, containing (R)- and (S)-stereochemistry. For example,

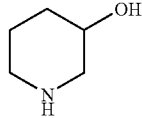

means containing both

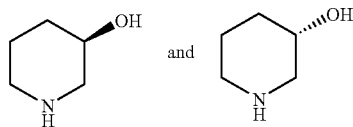

A dashed line ----- represents an optional bond.

Lines drawn into the ring systems, such as, for example:

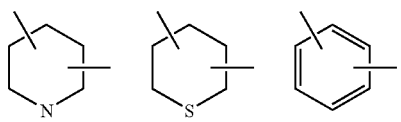

indicate that the indicated line (bond) may be attached to any of the substitutable ring atoms, non-limiting examples include carbon, nitrogen and sulfur ring atoms.

As well known in the art, a bond drawn from a particular atom wherein no moiety is depicted at the terminal end of the bond indicates a methyl group bound through that bond to the atom, unless stated otherwise. For example:

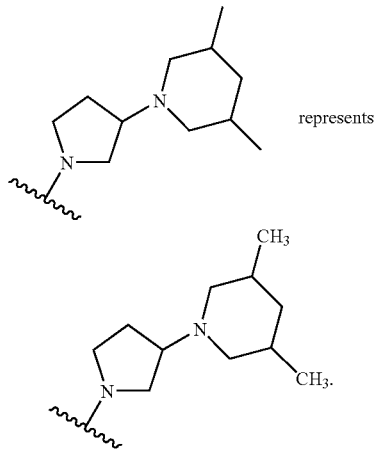

It should also be noted that any heteroatom with unsatisfied valences in the text, schemes, examples and Tables herein is assumed to have the hydrogen atom to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, R$^2$, etc.) occurs more than one time in any constituent or formula, its definition on each occurrence is independent of its definition at every other occurrence.

Unless defined otherwise, all definitions for the variables follow the convention that the group to the right forms the point of attachement to the molecule; i.e., if a definition is arylalkyl, this means that the alkyl portion of the definition is attached to the molecule.

Further, all divalent variable are attached from left to right. For example when R$^2$ is —(CH$_2$)$_q$N(R$^7$)YR$^{7'}$, and Y is —C(═O)NR$^7$—, then R$^1$ forms the group —(CH$_2$)$_q$N(R$^7$)—C(═O)N(R$^7$)—R$^{7'}$.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

For example, if a compound of Formula I or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-(C1-C2)alkyl and piperidino-, pyrrolidino- or morpholino$(C_2-C_3)$ alkyl, and the like.

Similarly, if a compound of Formula I contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, —P(O)(OH)$_2$, —P(O)(O$(C_1-C_6)$alkyl)$_2$ or glycosyl (the radical resulting from the removal of a hydroxyl group of the hemiacetal form of a carbohydrate), and the like.

If a compound of Formula I incorporates —NH— functional group, such as in a primary or secondary amine or in a nitrogen-containing heterocycle, such as imidazole or piperazine ring, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy $(C_1-C_6)$alkyl, amino $(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of illustrative solvates include ethanolates, methanolates, and the like. "Hydrate" is a solvate wherein the solvent molecule is H$_2$O.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Metabolic conjugates, such as glucuronides and sulfates which can undergo reversible conversion to the compounds of Formula I are contemplated in the present invention.

"Effective amount" or "therapeutically effective amount" is meant to describe an amount of compound or a composition of the present invention effective in producing the desired therapeutic, ameliorative, inhibitory or preventative effect.

The terms "purified", "in purified form" or "in isolated and purified form," as used herein, for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

"Capsule" is meant to describe a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

"Tablet" is meant to describe a compressed or molded solid dosage form containing the active ingredients with suitable diluents. The tablet can be prepared by compression of mixtures or granulations obtained by wet granulation, dry granulation or by compaction.

"Oral gels" is meant to describe to the active ingredients dispersed or solubilized in a hydrophillic semi-solid matrix.

"Powders for constitution" refers to powder blends containing the active ingredients and suitable diluents which can be suspended in water or juices.

"Diluent" refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

"Disintegrants" refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

"Binders" refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

"Lubricant" is meant to describe a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

"Glidents" means materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

"Coloring agents" refers to excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

"Bioavailability" refers to the rate and extent to which the active drug ingredient or therapeutic moiety is absorbed into the systemic circulation from an administered dosage form as compared to a standard or control. Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formulae Ia or Ib contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons or sulfurs on various substituents, including enantiomeric forms (which may exist even in the absence of asymmetric carbons), rotameric forms, atropisomers, and diastereomeric forms, are contemplated within the scope of this invention. For example, if a compound of Formula I incorporates a double bond or a fused ring, both the cis- and trans-forms, as well as mixtures, are embraced within the scope of the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula I may be atropisomers (e.g., substituted biaryls) and are considered as part of this invention. Enantiomers can also be separated by use of chiral HPLC column.

Polymorphic forms of the compounds of Formula I, and of the salts, solvates and prodrugs of the compounds of Formula I, are intended to be included in the present invention The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labelled reagent for a non-isotopically labelled reagent.

The compounds according to the invention have pharmacological properties; in particular, the compounds of Formula I can be useful as α2C adrenoreceptor agonists.

A preferred dosage is about 0.001 to 500 mg/kg of body weight/day of the compound of Formula I. An especially preferred dosage is about 0.01 to 25 mg/kg of body weight/day of a compound of Formula I, or a pharmaceutically acceptable salt or solvate of said compound.

The compounds of this invention may also be useful in combination (administered together or sequentially) with one or more therapeutic agents such as, for example, glucocorticosteroids, PDE-4 inhibitors, anti-muscarinic agents, cromolyn sodium, $H_1$ receptor antagonists, 5-$HT_1$ agonists, NSAIDs, angiotensin-converting enzyme inhibitors, angiotensin II receptor agonists, β-blockers, β-agonists (including both long and short acting), leukotriene antagonists, diuretics, aldosterone antagonists, ionotropic agents, natriuretic peptides, pain management/analgesic agents, anti-anxiety agents, anti-migraine agents, and therapeutic agents suitable for treating heart conditions, psychotic disorders, and glaucoma. Suitable steroids include prednisolone, fluticasone (including all ester such as the propionate or furoate esters), triamcinolone, beclomethasone, mometasone (including any ester form such as mometasone furoate), budasamine, ciclesonide betamethasone, dexamethasone, prednisone, flunisolide, and cortisone.

Suitable PDE-4 inhibitors include roflumilast, theophylline, rolipram, piclamilast, cilomilast and CDP-840.

Suitable antiimuscarinic agents include ipratropium bromide and tiatropium bromide.

Suitable $H_1$ antagonists include astemizole, azatadine, azelastine, acrivastine, brompheniramine, cetirizine, chlorpheniramine, clemastine, cyclizine, carebastine, cyproheptadine, carbinoxamine, descarboethoxyloratidine, diphenhydramine, doxylamine, dimethindene, ebastine, epinastine, efletirizeine, fexofenadine, hydroxyzine, ketotifen, loratidine, levocabastine, meclizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

Suitable anti-inflammatory agents include aspirin, diclofenac, diflunisal, etodolac, flurbiprofen, ibuprofen, indomethacin, ketoprofen, ketorolac, nabumetone, naproxen, oxaprozin, piroxicam, sulindac, and tolmetin.

Suitable aldosterone antagonists include spironolactone.

Suitable ionotropic agents include digitalis.

Suitable angiotensin II receptor agonists include irbesartan and losartan.

Suitable diuretics include spironolactone, methyclothiazide, bumetanide, torsemide, hydroflumethiazide, trichlormethiazide, hydroclorothiazide, triamterene, ethacrynic acid, methyclothiazide, hydrochlorothiazide, benzthiazide, hydrochlorothiazide, quinethazone, hydrochlorothiazide, chlorthalidone, furosemide, indapamide, hydroclorothiazide, triamterene, trichlormethiazide, hydrochlorothiazide, amiloride HCl, amiloride HCl, metolazone, trichlormethiazide, bendroflumethiazide, hydrochlorothiazide, polythiazide, hydroflumethiazide, chlorthalidone, and metolazone.

Suitable pain management/analgesic agents include Celecoxib, amitriptyline, ibuprofen, naproxen, gabapentin, tramadol, rofecoxib, oxycodone HCl, acetaminophenoxycodone HCl, carbamazepine, amitriptyline, diclofenac, diclofenac, etodolac, fenoprofen calcium, flurbiprofen, ibuprofen, indomethacin, ketoprofen, ketorolac tromethamine, mefenamic acid, meloxicam, nabumetone, naproxen, oxaprozin, piroxicam, sulindac, tolmetin sodium, valdecoxib, diclofenac/misoprostol, oxycontin, vicodin, darvocet, percocet, morphine sulfate, dilaudid, stadol, stadol NS, acetaminophen with codeine, acetaminophen with codeine #4, Lidoderm® patches, ziconotide, duloxetine, roboxetine, gabapentin and pregabalin.

Suitable β-blockers include acebutolol, atenolol, atenolol/chlorthalidone, betaxolol, bisoprolol fumarate, bisoprolol/HCTZ, labetolol, metoprolol tartrate, nadolol, pindolol, propranolol, propranolol/HCTZ, sotalol, and timolol.

Suitable β-agonists include dobutamine, ritodrine, salbutamol, levalbuterol, metaproternol, formoterol, fenoterol, bambuterol, brocaterol, clenbuterol, terbutaline, tulobuterol, epinephrine, isoprenalin, and hexoprenalin.

Suitable leucotriene antagonists include levamisole.

Suitable anti-migraine agents include rovatriptan succinate, naratriptan HCl, rizatriptan benzoate, sumatriptan succinate, zolmitriptan, almotriptan malate, methysergide maleate, dihydroergotamine mesylate, ergotamine tartrate, ergotamine tartrate/caffeine, Fioricet®, Fiorninal®, Depakene®, and Depakote®.

Suitable anti-anxiety and anti-depressant agents include amitriptyline HCl, bupropion HCl, citalopram hydrobromide, clomipramine HCl, desipramine, fluoxetine, fluvoxamine maleate, maprotiline HCl, mirtazapine, nefazodone HCl, nortriptyline, paroxetine HCl, protriptyline HCl, sertraline HCl, doxepin, and trimipramine maleate.

Suitable angiotensin converting enzyme inhibitors include Captopril, enalapril, enalapril/HCTZ, lisinopril, lisinopril/HCTZ, and Aceon®.

The pharmacological properties of the compounds of this invention may be confirmed by a number of pharmacological assays. The exemplified pharmacological assays which are described later have been carried out with the compounds according to the invention and their salts.

This invention is also directed to pharmaceutical compositions which comprise at least one compound of Formula I, or a pharmaceutically acceptable salt or solvate of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions or suspensions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formulae Ia or Ib, or a pharmaceutically acceptable salt or solvate of said compound and a pharmaceutically acceptable carrier, vehicle or diluent.

Yet another aspect of this invention is a kit comprising an amount of at least one compound of Formulae Ia or Ib, or a pharmaceutically acceptable salt or solvate of said compound and an amount of at least one therapeutic agent listed above, wherein the amounts of the two or more ingredients result in desired therapeutic effect.

In general, the compounds in the invention may be produced by a variety of processes know to those skilled in the art and by know processes analogous thereto. The invention disclosed herein is exemplified by the following preparations and examples which should not be construed to limit the scope of the disclosure. Alternative mechanistic pathways and analogous structures will be apparent to those skilled in the art. The practitioner is not limited to these methods.

One skilled in the art will recognize that one route will be optimized depending on the choice of appendage substituents. Additionally, one skilled in the art will recognize that in some cases the order of steps has to be controlled to avoid functional group incompatability.

The prepared compounds may be anyalyzed for their composition and purity as well as characterized by standard analytical techniques such as, for example, elemental anyalysis, NMW, mass spectroscopy and IR spectra.

One skilled in the art will recognize that reagents and solvents actually used may be selected from several reagents and solvents well known in the art to be effective equivalents. Hence, when a specific solvent or reagent is mentioned, it is meant to be an illustrative example of the conditions desirable for that particular reaction scheme and in the preparations and examples described below.

Where NMR data are presented, $^1$H spectra were obtained on either a Varian VXR-200 (200 MHz, $^1$H), Varian Gemini-300 (300 MHz), Varian Mercury VX-400 (400 MHz), or Bruker-Biospin AV-500 (500 MHz), and are reported as ppm with number of protons and multiplicities indicated parenthetically. Where LC/MS data are presented, analyses was performed using an Applied Biosystems API-100 mass spectrometer and C18 column, 10-95% $CH_3CN$—$H_2O$ (with 0.05% TFA) gradient. The observed parent ion is given.

The following solvents and reagents may be referred to by their abbreviations in parenthesis:

Me=methyl; Et=ethyl; Pr=propyl; Bu=butyl; Ph=phenyl, and Ac=acetyl
μl=microliters
AcOEt or EtOAc=ethyl acetate
AcOH or HOAc=acetic acid
ACN=acetonitrile
atm=atmosphere
BINAP=2,2'-bis(diphenylphosphino)-1,1'-binaphthalene
Bn=benzyl
Boc or BOC=tert-butoxycarbonyl
Cpd=compound
DAST=diethylaminosulfur trifluoride
dba=dibenylideneacetone
DCM or $CH_2Cl_2$: dichloromethane:
DMAP=4-dimethylaminopyridine
DMF=dimethylformamide
DMS=dimethylsulfide
DMSO=dimethyl sulfoxide
EDCl=1-(3-dimethylaminopropyl)-3-ethylcarbodiimide
eq=equivalent
g=grams
h or hr=hour
LAH=lithium aluminum hydride
LCMS=liquid chromatography mass spectrometry
min=minute
mg=milligrams
mL=milliliters
mmol=millimoles
MeOH: methanol
MS=mass spectrometry
NMR=nuclear magnetic resonance spectroscopy
RT or rt=room temperature (ambient, about 25° C.).
TBAF=tert-butylammonium floride
TBS=tert-butyldimethylsilyl
TEA or $Et_3N$=triethylamine
TFA=trifluoroacetic acid
THF=tetrahydrofuran
TLC=thin layer chromatography
TMS=trimethylsilyl
Tr=triphenylmethyl

EXAMPLES

The compounds of this invention can be prepared through the general approach outlined in Schemes 1-5. These schemes are being provided to illustrate the present invention. Group A is defined in these schemes in accordance with the definition in the invention; i.e., as an optionally substituted 5-membered heteroaryl, heterocyclyl or heterocyclenyl ring containing 1-3 heteroatoms. The depiction of A as an unsubstituted imidazole is not in any way to be considered a limitation of the invention scope.

Scheme 1 shows an approach in which S1 is acylated via a Friedel-Crafts or other related methodology to provide S2, wherein $R^4$ is H, Me or higher alkyl. Compound S2 is then reacted with A-Y (wherein A=optionally protected imidazole, heteroaryl, heterocyclyl or heterocyclenyl and Y=I, Br, Cl or other appropriate group) via a Grignard or related metal-facilitated addition. In various embodiments, the resulting alcohol S3 may be directly reduced via a a deoxygenation, such as, for example, $Et_3SiH$/TFA, $NaI/Me_2SiCl_2$ or other appropriate method. Alternatively, when $R^4$ is Me or higher alkyl, alcohol S3 may be eliminated to an olefin and subsequently reduced by hydrogenation or the like. Deprotection of the A group may be necessary depending on the nature of the group. For example, when A is a trityl or BOC-protected imidazole, deprotection under acidic conditions (TFA/$EtSi_3H$ or HCl/MeOH) is undertaken.

SCHEME 1:

S1

S2
$R^4$ = H or alkyl

S3                    S4 where A = optionally substituted (e.g., $R^5$ or a protecting group) heteroaryl (e.g., imidazole), heterocyclyl, or heterocyclenyl.

According to another embodiment (Scheme 2), compound S1 is converted to S5 and then reacted with A-Y. Subsequent reduction and/or elimination steps yield structures represented by S6.

SCHEME 2:

S1

S5

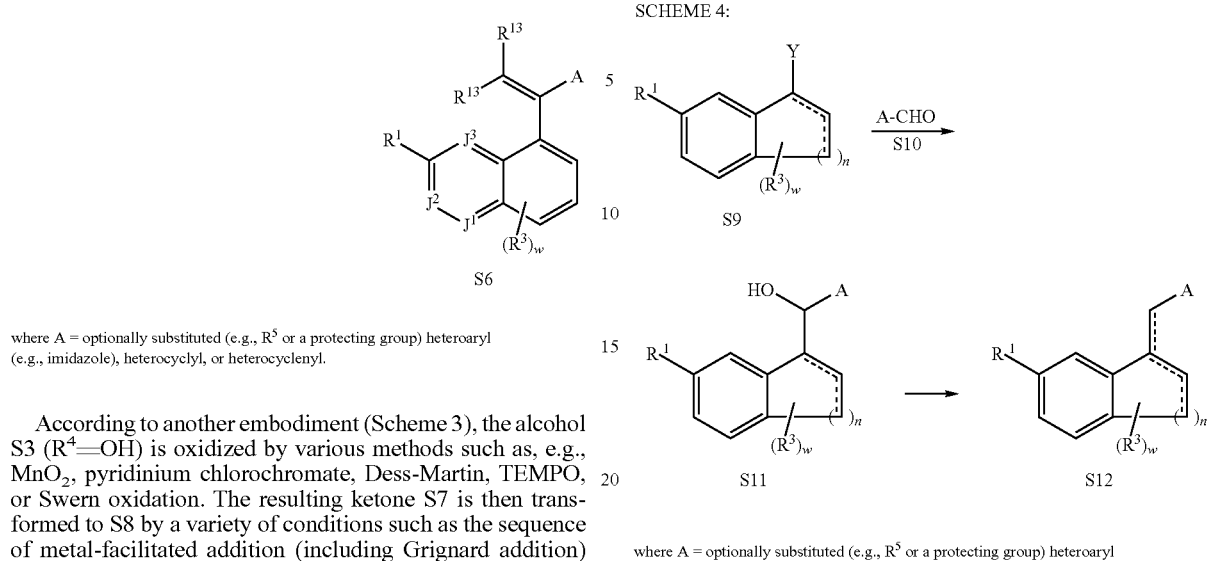

where A = optionally substituted (e.g., $R^5$ or a protecting group) heteroaryl (e.g., imidazole), heterocyclyl, or heterocyclenyl.

According to another embodiment (Scheme 3), the alcohol S3 ($R^4$=OH) is oxidized by various methods such as, e.g., $MnO_2$, pyridinium chlorochromate, Dess-Martin, TEMPO, or Swern oxidation. The resulting ketone S7 is then transformed to S8 by a variety of conditions such as the sequence of metal-facilitated addition (including Grignard addition) and elimination (including acid or base treatment with or without alcohol activation). Alternatively, this step is accomplished by direct olefin synthesis including e.g., Wittig, Horner-Emmons, Peterson, or other related methods.

SCHEME 3:

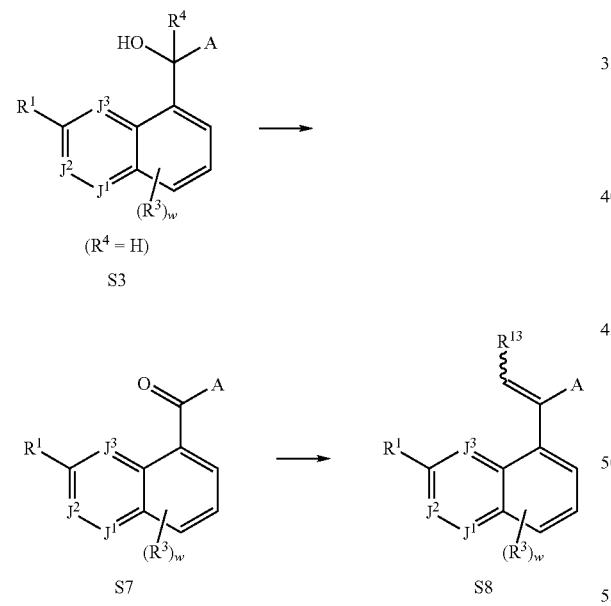

where A = optionally substituted (e.g., $R^5$ or a protecting group) heteroaryl (e.g., imidazole), heterocyclyl, or heterocyclenyl.

According to another embodiment (Scheme 4), compound S9 (wherein the indicated bonds may be saturated or unsaturated, n=1-3, and Y is Cl, Br, I or another appropriate group) undergoes metal-facilitated activation (such as, e.g., Grignard, Lithium base or related approaches) and subsequent reaction with the aldehyde S10. Further elaboration to S12 may be accomplished by use of reduction or elimination reactions as described in either schemes.

SCHEME 4:

where A = optionally substituted (e.g., $R^5$ or a protecting group) heteroaryl (e.g., imidazole), heterocyclyl or heterocyclenyl.

According to another embodiment (Scheme 5), compound S13 is converted to S14 (n=0-2) using olefin synthesis methodology (such as Wittig, Horner-Emmons, Peterson, or other related methods). Hydrogenation and subsequent cyclization (see J. Med. Chem. 1997, 40, 3014) provides S16. Homologation to ketone or aldehyde S17 occurs via one of numerous methodologies including a Wittig/hydrolysis sequence, Horner-Emmons/hydrolysis or related approaches (see Synthesis, 1979, 633-664). Conversion to S18 occurs as described in earlier schemes.

SCHEME 5:

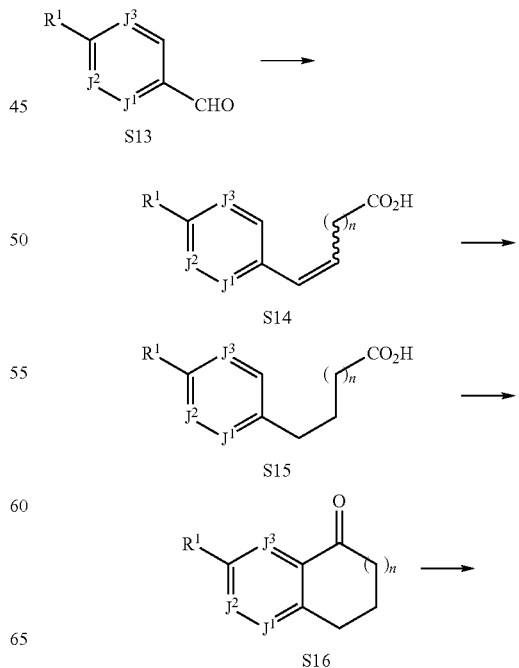

-continued

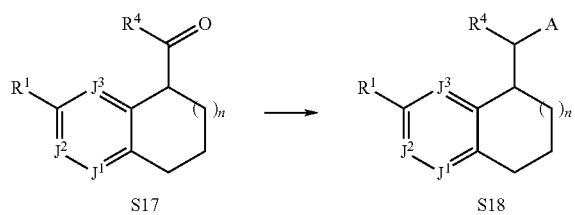

where A = optionally substituted (e.g., $R^5$ or a protecting group) heteroaryl (e.g., imidazole), heterocyclyl, or heterocyclenyl.

The starting materials and reagents described herein for preparing compounds described are either available from commercial suppliers such as Aldrich Chemical Co. (Wisconsin, USA) and Acros Organics Co. (New Jersey, USA) or are prepared by literature methods known to those skilled in the art.

Exemplary compounds are prepared as described in the examples below or from starting materials that are known in the art. These examples are being provided to further illustrate the present invention. They are for illustrative purposes only; the scope of the invention is not to be considered limited in any way thereby.

Example 1

1

Step 1

1A

A solution of 2-bromonaphthalene (12.6 g, 61.3 mmol) in DCM (100 mL) was treated with $AlCl_3$ (25 g, 190 mmol) at −10° C. and stirred until a dark green mixture was observed. The reaction was cooled to −78° C. and treated slowly with acetyl chloride (9.1 mL, 127 mmol). After 5 h, the reaction was warmed to 0° C. and treated slowly with aqueous HCl (1 M, 50 mL). After cessation of bubbling, the layers were separated. The aqueous layer was then extracted with $CH_2Cl_2$ (2×). The combined organic layers were dried over $Na_2SO_4$, filtered and concentrated to a clear oil. Chromatography (2-10% EtOAc/hex) provided 1A as a white solid.

Step 2

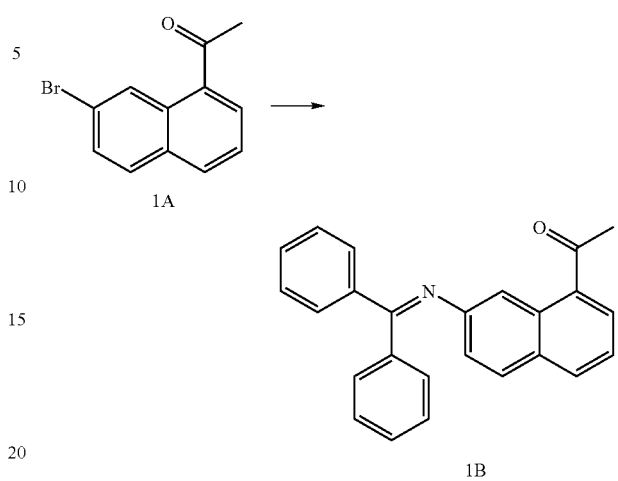

A flask containing compound 1A (500 mg, 2.0 mmol), $Pd_2(OAc)_2$ (45 mg, 0.2 mmol), BINAP (188 mg, 0.3 mmol) and $Cs_2CO_3$ (1.3 g, 4.0 mmol) was evacuated and filled with $N_2$ three times. Toluene (20 mL) and benzophenone imine (550 mg, 3.0 mmol) were sequentially added. The reaction was then stirred at 100° C. overnight. After cooling to RT, the precipitate was filtered and washed with $CH_2Cl_2$. The combined filtrate was concentrated and chromatographed (3-10% EtOAc/hex) to provide 1B as a yellow foam.

Step 3

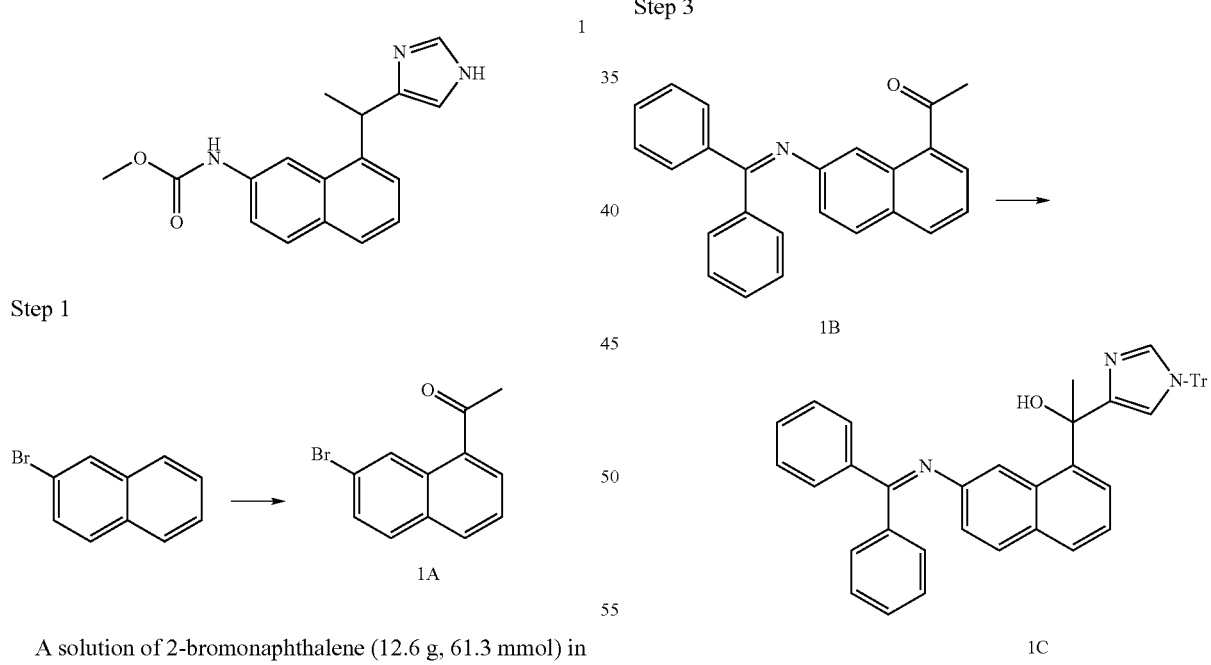

A solution of 4-iodo-1-tritylimidazole (433 mg, 0.99 mmol) in $CH_2Cl_2$ (8 mL) at 0° C. was treated slowly with EtMgBr (3 M in ether, 0.36 mL). The mixture was stirred at 0° C. for 0.5 h and then warmed to RT. After 15 minutes, the reaction was added slowly to a stirred solution of 1B (330 mg, 0.94 mmol) in $CH_2Cl_2$ (2 mL) at 0° C. The mixture was stirred at 0° C. for 1.5 h and then stirred at RT overnight. The reaction was then cooled in an ice bath, quenched with saturated aqueous $NH_4Cl$, and extracted with $CH_2Cl_2$ (3×). The combined organic layers were concentrated and chromatographed (20-50% EtOAc/hex) to provide 1C as a yellow foam (44%).
Step 4

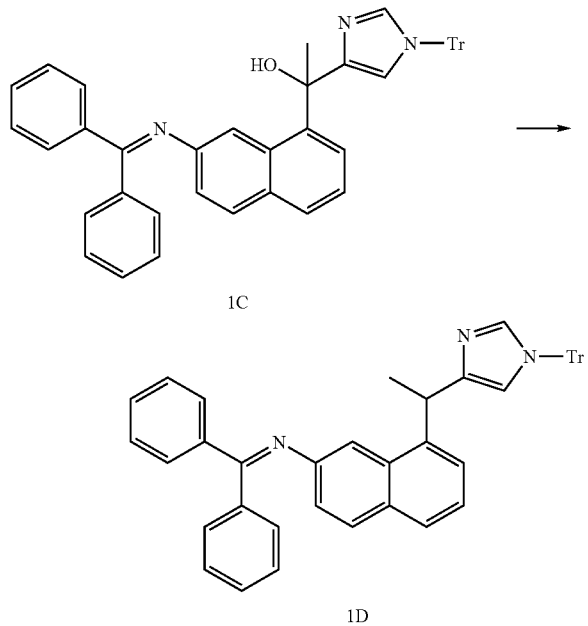

1C

1D

A mixture of NaI (245 mg, 1.64 mmol) in MeCN (5 mL) was treated with Me₂SiCl₂ (0.1 mL, 0.8 mmol) to give a white cloudy solution. A solution of alcohol 1C (150 mg, 0.23 mmol) in CH₂Cl₂ (5 mL) was then added dropwise. The resulting red solution was stirred for 0.5 h. The reaction was diluted with CH₂Cl₂ (30 mL), washed with NaOH (1N), dried over Na₂SO₄, filtered and concentrated. Chromatography (10-50% EtOAc/hex) provided 1D.
Step 5

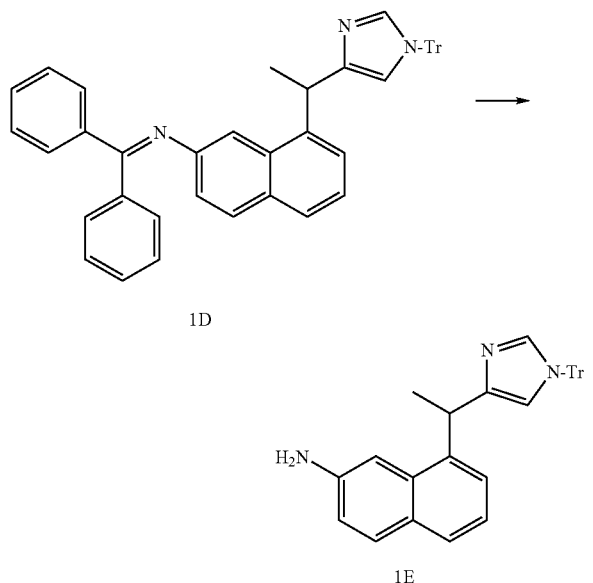

1D

1E

A mixture of 1D (160 mg, 0.25 mmol), NaOAc (98 mg, 1.2 mmol), and NH₂OH—HCl (62 mg, 0.89 mmol) in MeOH (5 mL) was stirred at RT overnight. The reaction was then treated with aqueous NaOH (1 N, 10 mL) and extracted CH₂Cl₂ (2×). The combined organic extracts were dried over Na₂SO₄, filtered and concentrated. Chromatography (20-50% EtOAc/hex) provided 1E as a white foam.
Steps 6-7

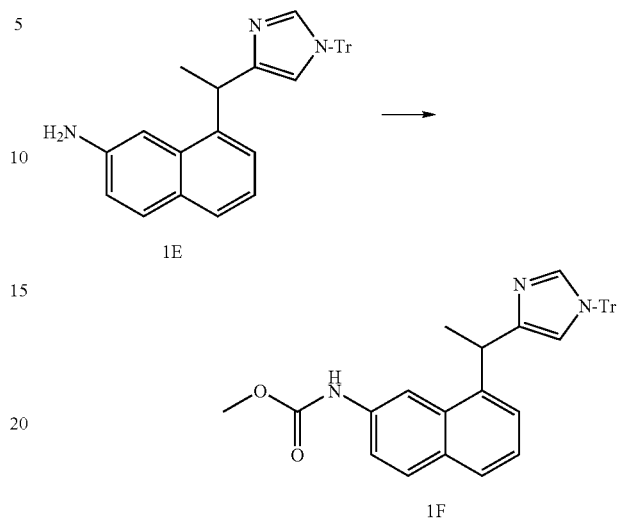

1E

1F

A solution of 1E (60 mg, 0.12 mmol) in THF (5 mL) was treated with Et₃N (50 μL, 0.38 mmol) and then cooled to 0° C. Methyl chloroformate (15 μL, 0.19 mmol) was then added. After stirring for 30 min at 0° C., the reaction was treated with H₂O and extracted with CH₂Cl₂ (3×). The combined organic extracts were dried over Na₂SO₄, filtered and concentrated. Chromatography (20-50% EtOAc/hex) provided 1F as a white foam.

A solution of 1F (60 mg, 0.11 mmol) in CH₂Cl₂ (5 mL) was treated with TFA (0.22 mL, 2.79 mmol) and Et₃SiH (45 μL, 0.28 mmol) and then stirred 3 h. The reaction was then concentrated in vacuo. Chromatography (1-5% of 7N NH3-MeOH in CH₂Cl₂) provided the title compound 1. MS m/z 296 (MH⁺).

Example 2

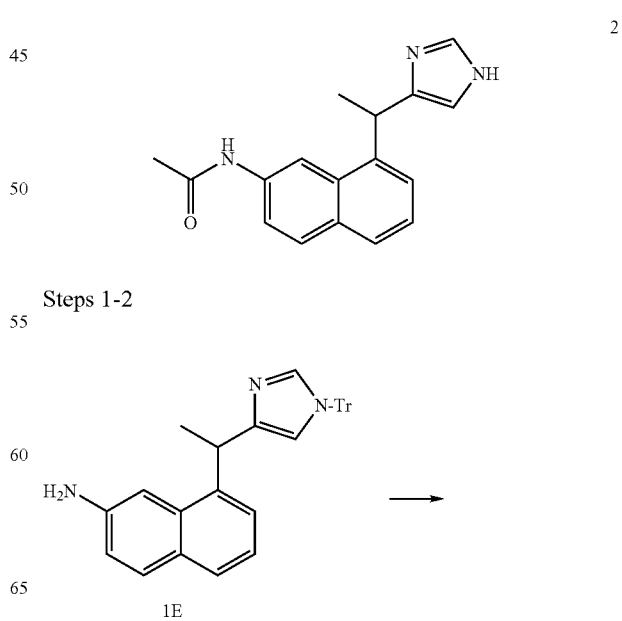

2

Steps 1-2

1E

-continued

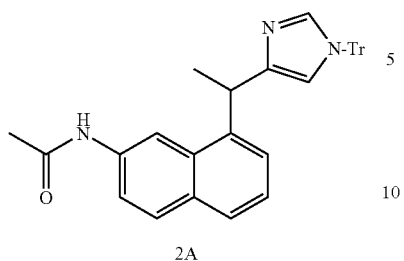

2A

A solution of 1E in THF is treated with Et₃N and Ac₂O to provide 2A In a similar manner that described in Example 1 (Step 7), compound 2A is treated with TFA and Et₃SiH to provide the title compound 2.

In a similar manner that described above, the following compounds are synthesized from 1E by using the indicated reagent:

| Cpd | Structure | Reagent |
|-----|-----------|---------|
| 2B | 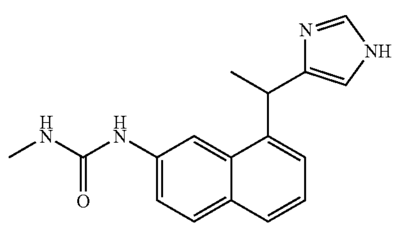 | MeNCO |
| 2C | 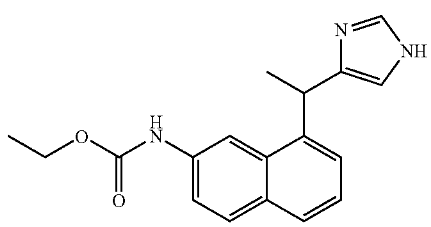 | ClCO₂Et |
| 2D | 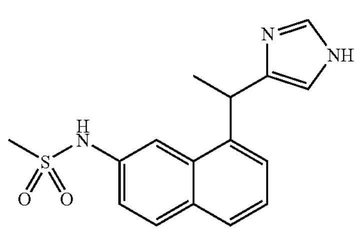 | SO₂Cl |
| 2E | 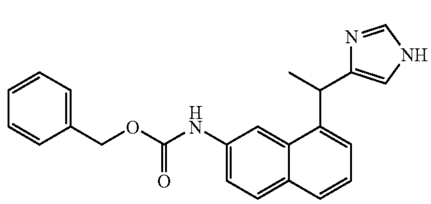 | ClCO₂Bn |

Example 3

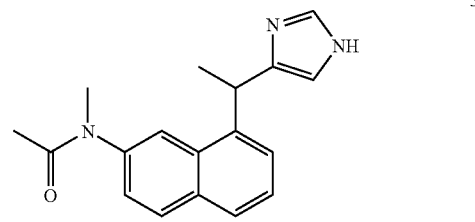

3

Step 1

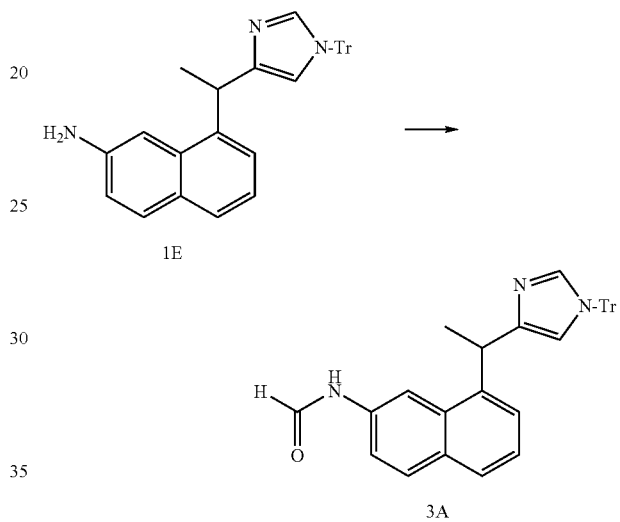

Compound 1E is treated with a mixture of Ac₂O/HCO₂H or alternatively heated in ethyl formate or butyl formate overnight to obtain 3A.

Steps 2-4

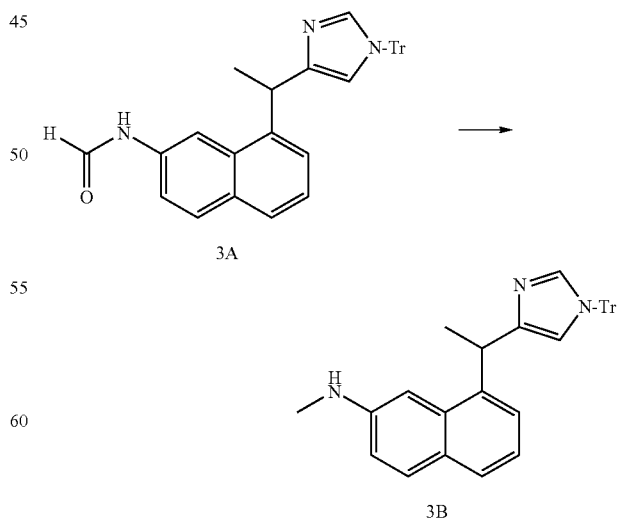

A mixture of 3A in THF or the like is treated with BH₃-DMS and heated to obtain 3B. In a manner similar to Example 1 (Steps 6-7), 3B is sequentially treated with acetyl chloride and TFA-Et₃SiH to yield the title compound 3.

In a similar manner that described above, the following compounds are synthesized from 3B by using the indicated reagent:

| Cpd | Structure | Reagent |
|---|---|---|
| 3C | 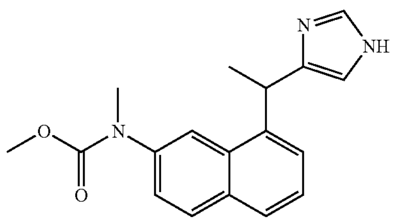 | ClCO₂Me |
| 3D | 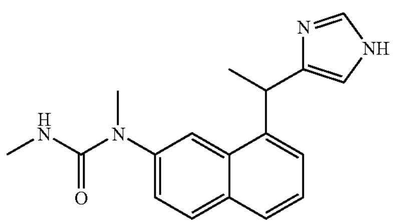 | MeNCO |
| 3E | 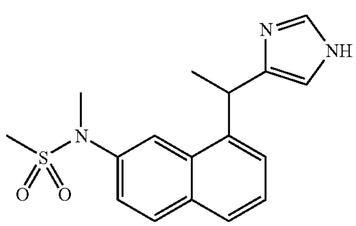 | SO₂Cl |
| 3F | 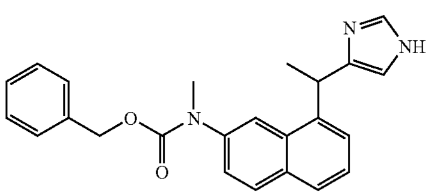 | ClCO₂Bn |

Example 4

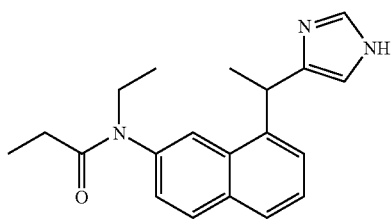

Steps 1-3

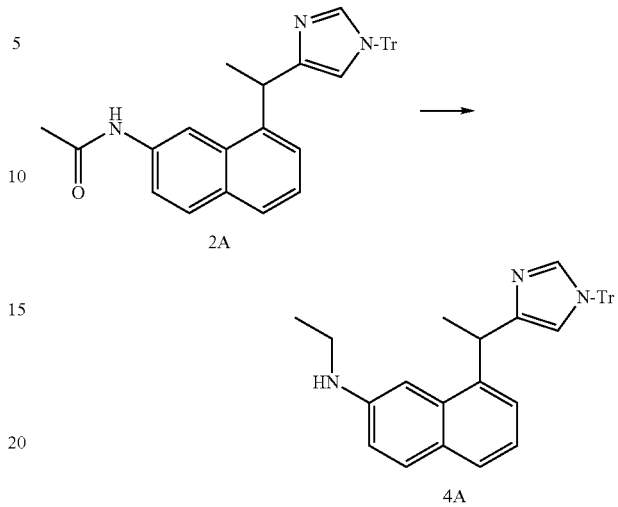

In a similar manner that described Example 3 (Step 2), 2A is reduced with BH₃-DMS to yield 4A. Alternatively, 4A is obtained via hydrogenation of compound 1E in the presence of 10% Pd/C and MeCN in MeOH.

Sequential treatment with propionyl chloride and TFA/Et₃SiH as described in Example 1 (Steps 6-7) provides 4 from compound 4A.

In a similar manner that described above, the following compounds are synthesized from 4A and the indicated reagent, followed by TFA deprotection.

| Cpd | Structure | Reagent |
|---|---|---|
| 4B | 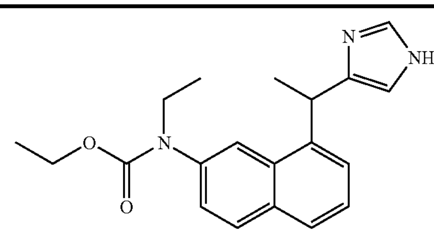 | ClCO₂Et |
| 4C | 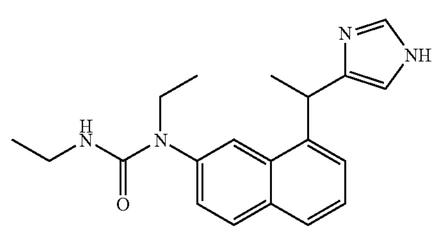 | EtNCO |
| 4D | 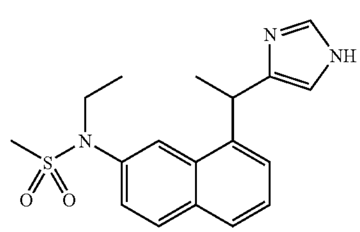 | SO₂Cl |

| Cpd | Structure | Reagent |
|---|---|---|
| 4E | 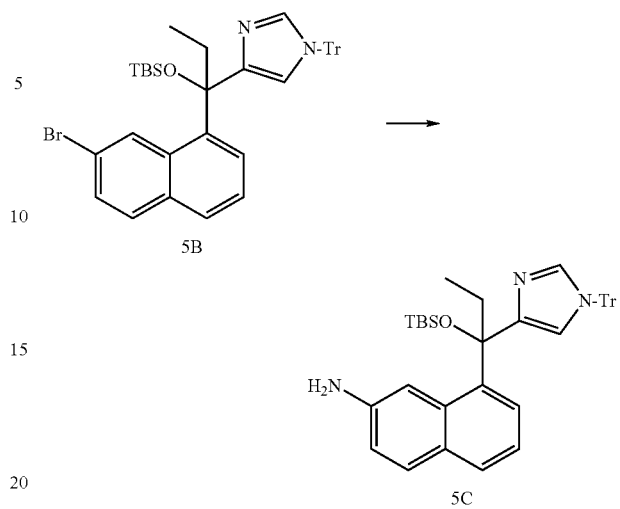 | ClCO$_2$Bn |

Example 5

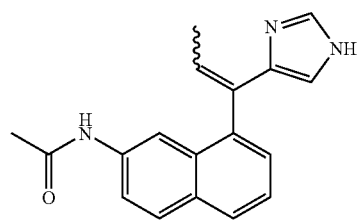

Step 1

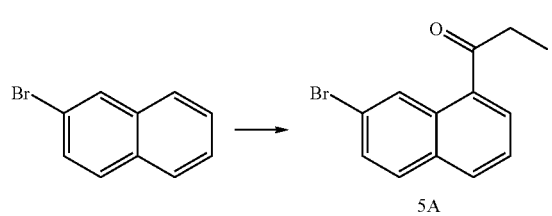

In a manner similar to that described in Example 1 (Step 1), 2-bromonaphthalene is treated with AlCl$_3$ and propionyl chloride to provide 5A.

Steps 2-3

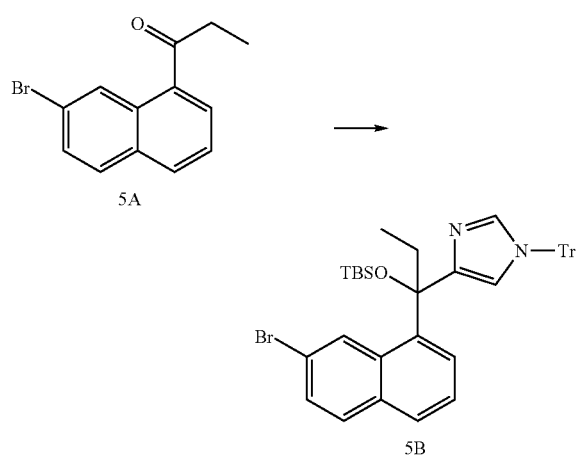

In a manner similar to that described in Example 1 (Step 3), 4-Iodo-1-tritylimidazole is treated with EtMgBr and then reacted with compound 5A. The resulting alcohol is subsequently protected with TBSCl/imidazole to afford compound 5B.

Steps 4-5

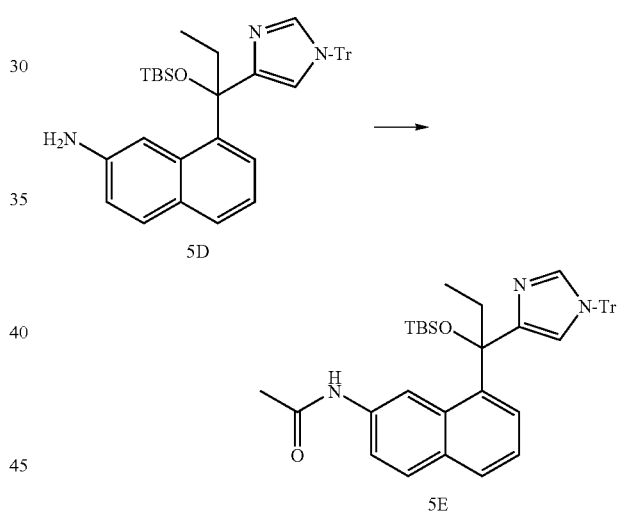

In a manner similar to that described in Example 1 (Steps 2 and 5), compound 5B is treated with benzophenone imine and Pd$_2$(OAc)$_2$ and then NH$_2$OH afford 5C.

Step 6

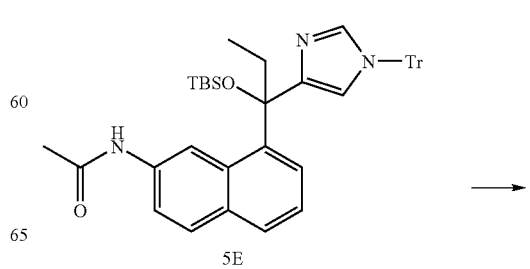

In a manner similar to that described in Example 1 (Step 6), compound 5D is acetylated with a reagent such as acetyl chloride or acetic anhydride to afford 5E. Alternatively, the transformation is accomplished with AcOH and a coupling agent, such as EDCl.

Steps 7-9

-continued

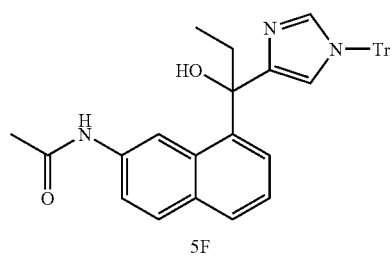

5F

Compound 5E is treated with TBAF or pyridine-HF to remove the TBS group to provide 5F. Concomitant elimination/deprotection with TFA or HCl/MeOH provides the title compound 5.

In a similar manner that described above, the following compounds are synthesized from 5D by using the indicated reagent in Step 6:

Alternatively, compound 5F is deoxygenated in a manner analogous to that described in Example 1 (Step 4) by treatment NaI/Me$_2$SiCl$_2$ Alternatively, compound 5F is deoxygenated in a manner analogous to that described in Example 9 (Steps 7-8) by sequential treatment with 1,1'-thiocarbonyldiimidazole/DMAP (40 mg, 0.31 mmol) and AlBN/Bu$_3$SnH.

Example 7

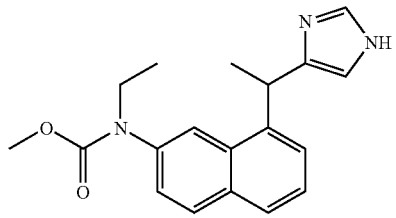

7

| Cpd | Structure | Reagent |
|---|---|---|
| 5G | 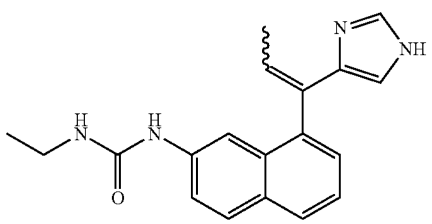 | EtNCO |
| 5H | 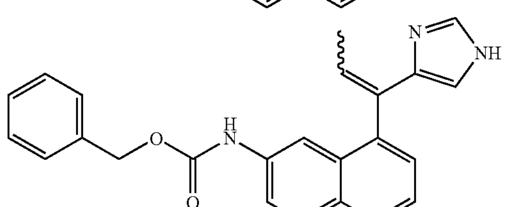 | ClCO$_2$CH$_2$Ph |
| 5I | 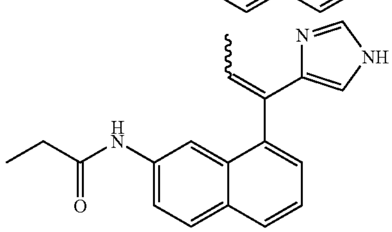 | ClCOEt |

Example 6

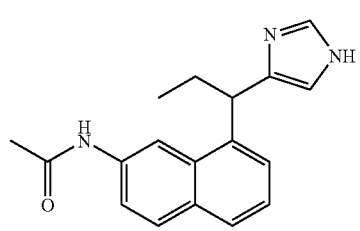

6

Compound 5 is hydrogenated with Pd(OH)$_2$/C or similar catalyst in MeOH or EtOAc to yield the title compound 6.

Step 1

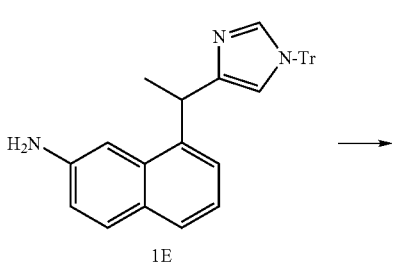

1E

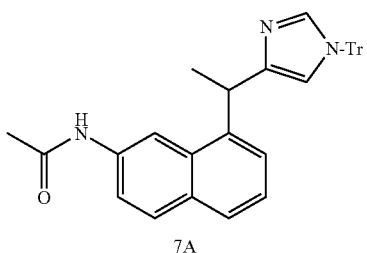

7A

To a solution of 1E (1.71 g, 3.56 mmol) in THF was added TEA (1.5 mL, 10.7 mmol), followed by AcCl (0.4 mL, 5.34 mmol). The reaction was stirred at RT for 30 min, treated with H$_2$O, and extracted with DCM (2×). The combined organic extracts were dried over Na$_2$SO$_4$, filtered and concentrated. Chromatography (2% MeOH/DCM, then 2% of 7N NH$_3$-MeOH in DCM) provided 7A as a light brown foam.

Step 2

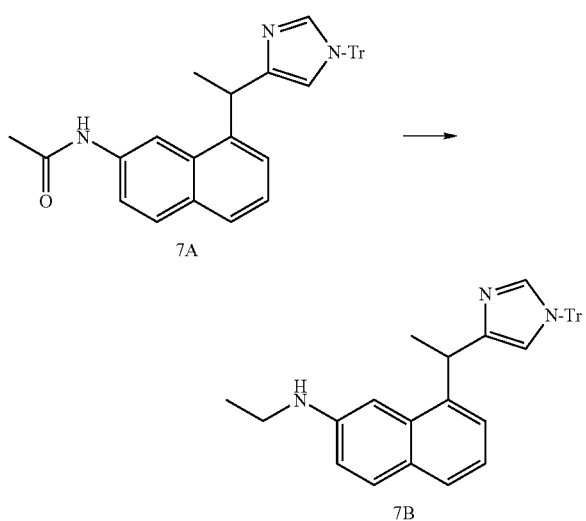

A solution of 7A (1.96 g, 3.75 mmol) in THF (50 mL) was treated with BH$_3$-DMS (2.8 mL, 2.0 M/THF) dropwise via a syringe, heated at reflux for 1 h, and then concentrated. K$_2$CO$_3$ (2.0 eq) and EtOH (20 mL) were then added. The mixture was refluxed for 30 min, cooled to RT, filtered and concentrated. The reaction was treated with water and extracted with DCM (2×). The combined organic layer was dried with Na$_2$SO$_4$, filtered and concentrated. Chromatography (10-20% EtOAc/hexanes) provided 7B as a light yellow solid.

Steps 3-4

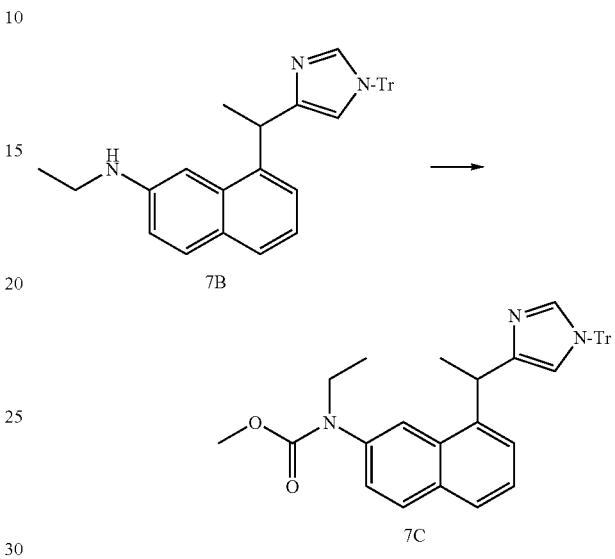

Compound 7B (190 mg, 0.374 mmol) was dissolved in THF (10 mL), treated with Et$_3$N (0.52 mL, 3.74 mmol) and ClCO$_2$Me (0.15 mL, 1.87 mmol), and heated at reflux overnight. The reaction was quenched with water and extracted with DCM (3×). The combined organic layer was dried over Na$_2$SO$_4$, filtered and concentrated. Chromatography (20-50% EtOAc/hexanes) gave 7C as a white foam.

A solution of 7C (110 mg, 0.190 mmol) in DCM (6 mL) was treated with TFA (0.7 mL, 9.50 mmol) and Et$_3$SiH (0.3 mL, 1.90 mmol), stirred at RT for 4 h and concentrated. Chromatography (2-5% of 7N NH$_3$-MeOH in DCM) gave the title compound 7 as a white foam. LCMS m/z 324 (MH+).

In a similar manner that described above in Steps 3 and 4, the following compounds 7D-7J were synthesized from 7B by using the indicated reagents, followed by deprotection with TFA and Et$_3$SiH.

| Cmpd | Reagents/Conditions | Structure | LCMS (MH+) |
|---|---|---|---|
| 7D | AcCl, Et$_3$N THF/RT | 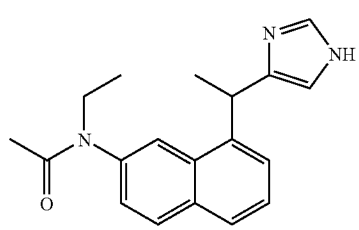 | 308 |

| Cmpd | Reagents/Conditions | Structure | LCMS (MH+) |
|---|---|---|---|
| 7E | CH₃OCH₂COCl, Et₃N THF/RT | 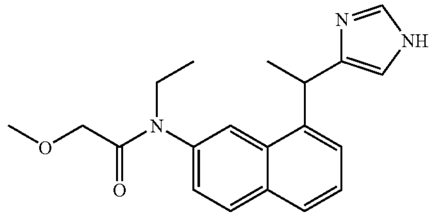 | 338 |
| 7F | CH₃OCH₂CH₂OCOCl Et₃N THF/Reflux | 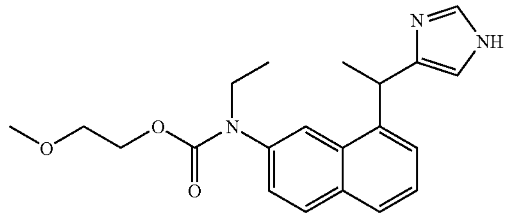 | 368 |
| 7G | MeNCO DCM/RT | 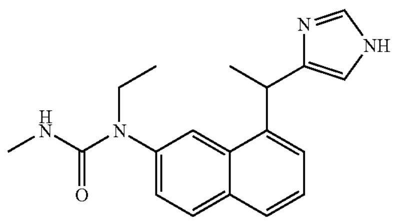 | 323 |
| 7H | PhCH₂NCO DCM/RT | 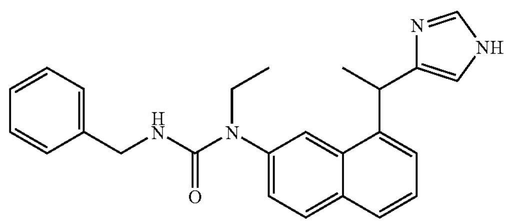 | 399 |
| 7I | 4-F-C₆H₄-CH₂-NCO DCM/RT | 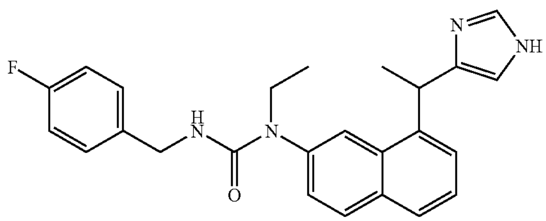 | 417 |
Example 8
Step 1
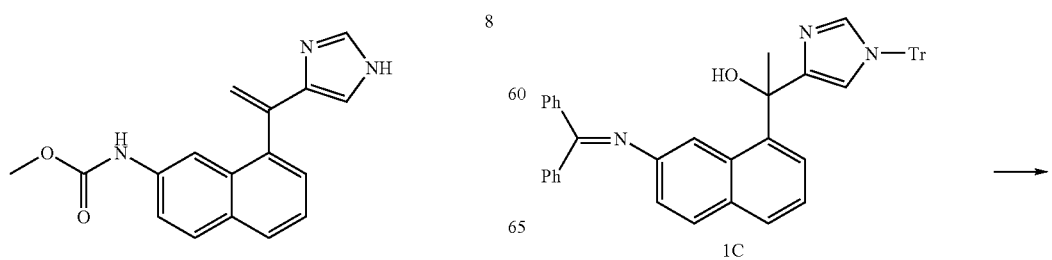

Step 2

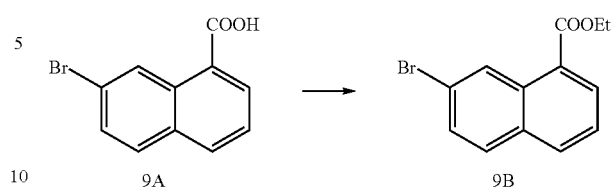

Compound 9A (17.8 g) was combined with AcCl (25 mL) in EtOH (500 mL) and refluxed overnight. The reaction was concentrated and treated with NaOH (10.0 g in 200 mL $H_2O$) and DCM. The mixture was extracted with DCM (4×). The combined extracts were dried over $Na_2SO_4$, filtered and concentrated. Chromatography (0-5% EtOAc/hexanes) gave 9B as a red oil.

Step 3

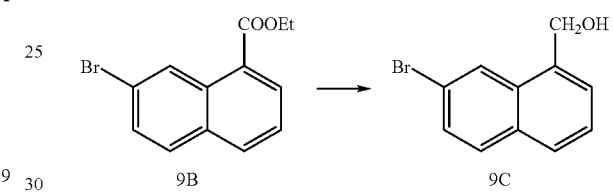

A solution of 9B (6.87 g, 24.6 mmol) in THF (100 mL) was cooled in an ice bath and then treated portionwise with LAH (1.03 g, 27.1 mmol). The reaction was stirred at 0° C. for 3 h. Water (1 mL) was added to quench the reaction at 0° C., followed by 1.0 N NaOH (1 mL) and another portion of $H_2O$ (3 mL). The mixture was filtered, concentrated and chromatographed (0-50% EtOAc/hexanes) to give 9C as a white solid.

Step 4

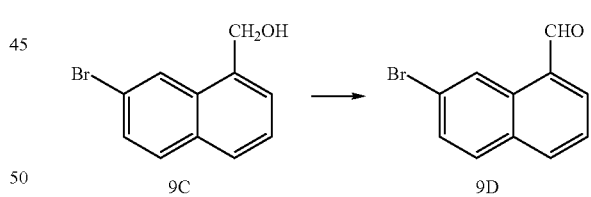

To a flame dried flask, oxalyl chloride (1.53 mL, 17.5 mmol) was dissolved in DCM (25 mL), cooled down to −70° C. DMSO (2.5 mL, 35.0 mmol) in DCM (6 mL) was added slowly via syringe, maintaining an internal temperature less than −60° C. during the addition. A solution of 9C (3.32 g, 14.0 mmol) in DCM (20 mL) was added to the above solution slowly via dropping funnel. The reaction was stirred at −70° C. for 1 h, treated with $Et_3N$ (5.9 mL, 42.0 mmol), and warmed to RT. The mixture was quenched with $H_2O$ and extracted with DCM (2×). The combined organic extracts were dried over $Na_2SO_4$, filtered and concentrated. Chromatography (5-10% EtOAc/hexanes) provided 9D as a light yellow solid.

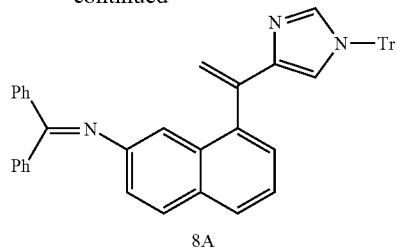

8A

A mixture of 1C (140 mg, 0.212 mmol) and DAST (65 μL, 0.531 mmol) in DCM, was stirred at RT overnight. The reaction was cooled in an ice bath and carefully quenched with $H_2O$. The layers were then separated. The aqueous layer was extracted DCM (2×). The combined DCM extracts were dried over $Na_2SO_4$ and concentrated. Chromatography (20% EtOAc/hexanes) provided 8A as a yellow foam.

Steps 2-4

In a manner similar to that described in Example 1 (Steps 5-7), compound 8A was sequentially deprotected with $NH_2OH$, reacted with $ClCO_2Me$, and deprotected with TFA to provide 8. LCMS m/z 294 (MH+).

Example 9

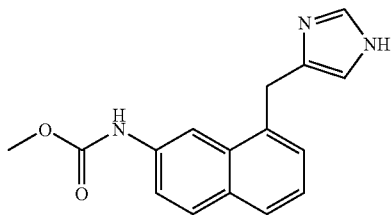

9

Step 1

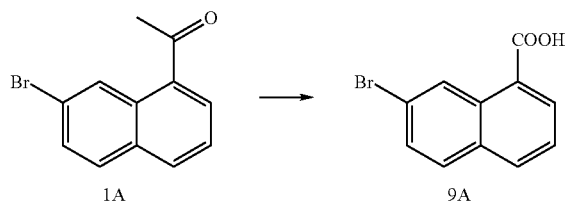

Compound 1A (13.5 g, 54.2 mmol) and t-BuOK (16.0 g, 135.5 mmol) were combined with t-BuOH (200 mL) to give a dark solution. $Na_2CO_3$-$1.5H_2O_2$ (11.1 g, 70.5 mmol) was added portionwise, followed by 1,3-dinitrobenzene (0.91 g, 5.42 mmol). The reaction was refluxed for 1 hr, cooled briefly, and treated with another portion of $Na_2CO_3$-$1.5H_2O_2$ (5.32 g, 33.9 mmol). The mixture was refluxed for another hour, cooled, treated with a third portion of $Na_2CO_3$-$1.5H_2O_2$ (5.32 g, 33.9 mmol) and refluxed overnight. The reaction was cooled to RT, concentrated, and treated with $H_2O$ (100 mL). After cooling in an ice bath, the mixture was slowly and carefully treated with 98% $H_2SO_4$ (30 mL) and then extracted with EtOAc (4×200 mL). The combined extracts were dried over $Na_2SO_4$, filtered and concentrated to give 9A as a dark foam, which was used in the next step without further purification.

Step 5

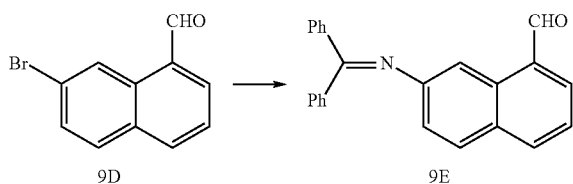

In a manner similar to that described in Example 1 (Step 2), 9D was converted to 9E.

Step 6

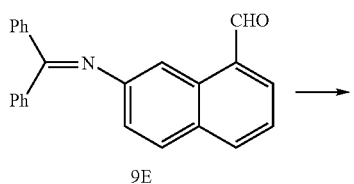

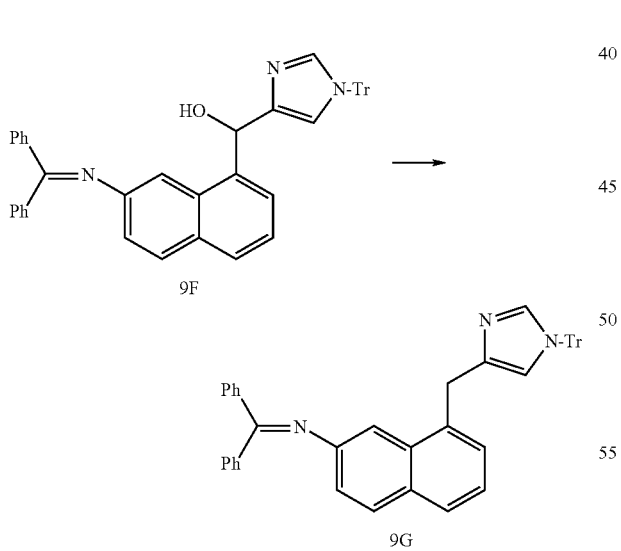

In a manner similar to that described in Example 1 (Step 3), 9E was converted to 9F.

Steps 7-8

A mixture of 9F (1.0 g, 1.55 mmol), 1,1'-thiocarbonyldi-imidazole (0.41 g, 2.32 mmol) and DMAP (40 mg, 0.31 mmol) in THF (20 mL) was refluxed for 2 h. Additional 1,1'-thiocarbonyldiimidazole (0.20 g, 1.16 mmol) and DMAP (20 mg, 0.16 mmol) was then added. The reaction was refluxed for another 2 h, stirred at RT overnight and quenched with sat. aq. NH$_4$Cl (20 mL). The mixture was then extracted with EtOAc (2×), dried over Na$_2$SO$_4$, filtered, concentrated and chromatographed (0-50% EtOAc/hexanes).

The resulting yellow foam (0.87 g, 1.15 mmol) was dissolved together with AIBN (50 mg, 0.29 mmol) in toluene (10 mL) and was added to a refluxing solution of Bu$_3$SnH (0.62 mL, 2.30 mmol) in toluene (20 mL). The reaction was refluxed overnight. The mixture was then concentrated, diluted with DCM (30 mL), washed with 1.0 N HCl (2×30 mL), sat. aq. NaHCO$_3$ (2×30 mL) and H$_2$O (1×50 mL). The organic extracts were dried over Na$_2$SO$_4$, filtered and concentrated and chromatographed (1-20% EtOAc/hexanes) to give 9G as a yellow foam.

Steps 9-11

In a manner similar to that found in Example 1 (Steps 5-7), 9G was sequentially deprotected with NH$_2$OH, reacted with ClCO$_2$Me, and deprotected with TFA to provide the title compound 9. LCMS m/z=282 (MH+).

Example 10

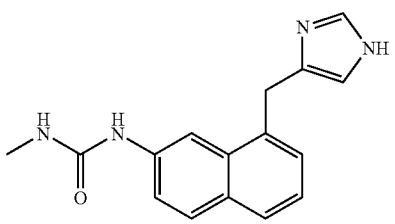

Step 1

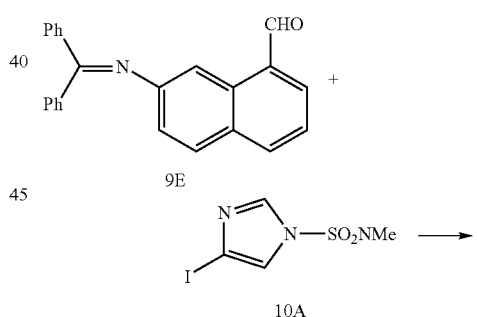

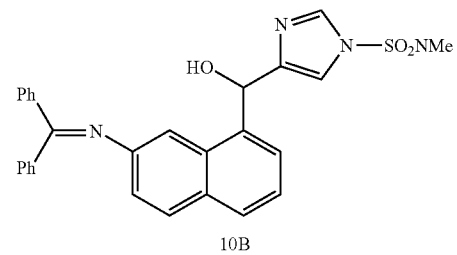

In a manner similar to that described in Example 1 (Step 3), 9E was reacted with 4-iodo-N,N-dimethyl-1H-imidazole-1-sulfonamide (10A) and EtMgBr to provide 10B.

Steps 2-3

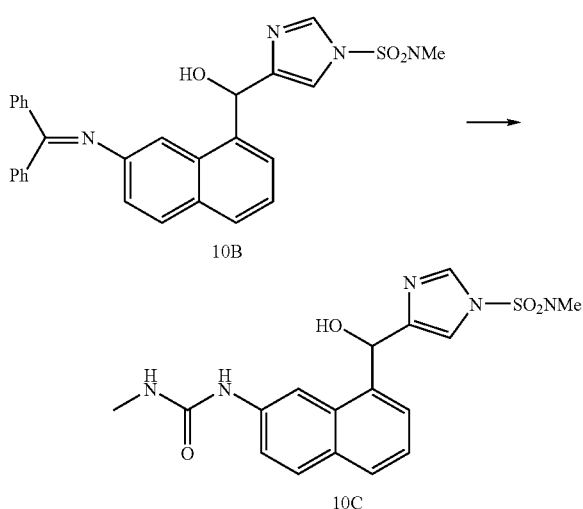

In a manner similar to that described in Example 1 (Step 5) and Example 7, 10B was deprotected with NH$_2$OH and reacted with MeNCO to provide 10C.

Steps 4-5

In a manner similar to Example 1 (Step 7), 10C was deoxygenated by treatment with Et$_3$SiH (10 eq.) and TFA (50 eq) at room temperature for 30 min. Final deprotection was accomplished by refluxing in 2M HCl-dioxane (3 h to overnight) to provide the title compound 10. LCMS m/z=281 (MH+).

Example 11

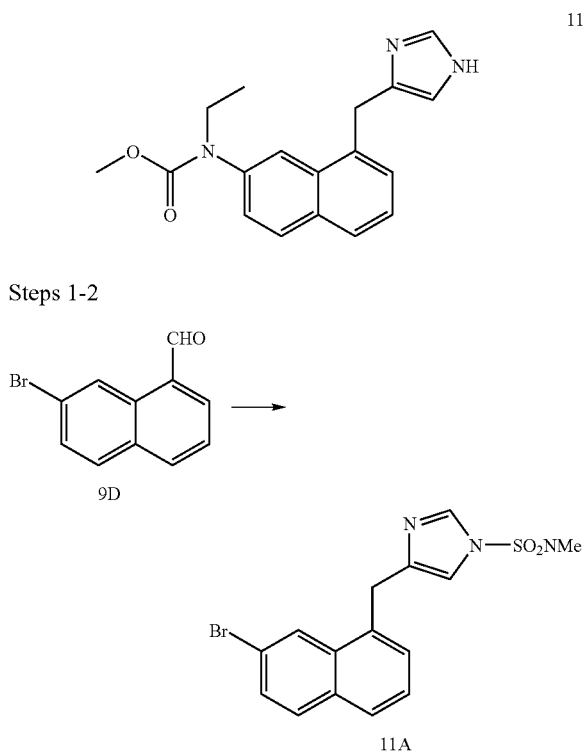

Steps 1-2 ethyl-1H-imidazole-1-sulfonamide (10A) and deoxygenated with Et$_3$SiH/TFA to provide 11A.

Step 3

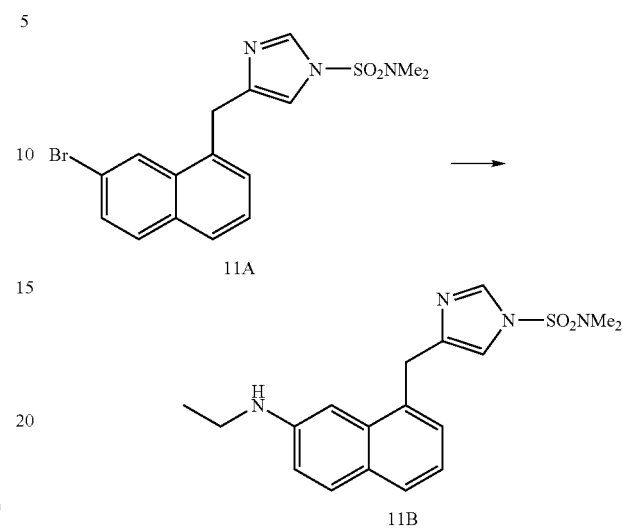

A sealed tube was charged with 11A (1.76 g, 4.46 mmol), K$_3$PO$_4$ (1.89 g, 8.92 mmol) and CuI (0.85 g, 4.46 mmol) and then degassed and filled with N$_2$ (3×). Ethylamine (2.0M/THF, 6.7 mL), 2-acetylcyclohexanone (0.6 mL, 4.46 mmol) and DMF (20 mL) were added. The reaction was heated at 100° C. overnight, and then concentrated. EtOAc and H$_2$O were added and the layers were separated. The organic layer was washed with brine (3×), dried over Na$_2$SO$_4$, filtered and concentrated. Chromatography (20-50% EtOAc/hexanes) provided 11B as a white foam.

Steps 4-5

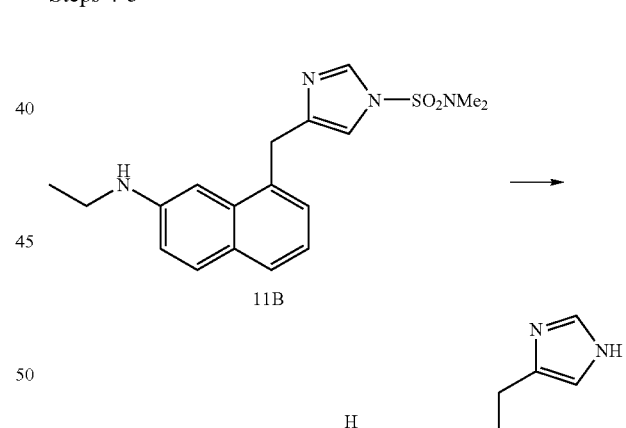

Refluxing 11B in 2M HCl-dioxane (3 h to overnight) provided compound 11C. LCMS m/z=252 (MH+).

In a manner similar to that described in Example 1 (Step 6), 11C was converted to the title compound 11 by treatment with ClCO$_2$Me, TEA, and DMAP (0.2 eq) in THF. LCMS m/z=310 (MH+).

In an analogous manner, compound 11D was synthesized by reacting 11C with 2-methoxyacetyl chloride, and DMAP. LCMS m/z=324 (MH+).

In a manner similar to that described in Example 10 (Steps 1 and 4), 9D was sequentially reacted with 4-iodo-N,N-dim-

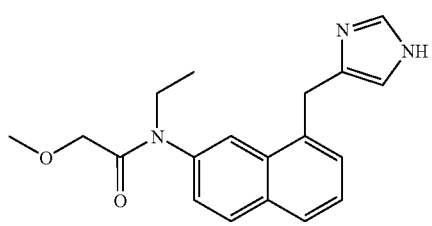

Example 12

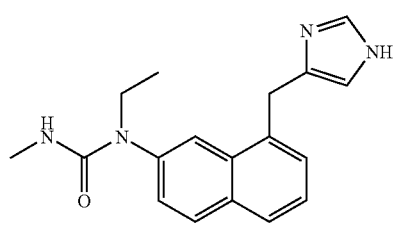

Step 1

A mixture of 11C (30 mg, 0.119 mmol), Boc$_2$O (39 mg, 0.179 mmol) and DMAP (3 mg, 0.024 mmol) in DCM (5 mL), was stirred at 0° C. for 1 h. The reaction was quenched with 1.0N NaOH (5 mL) and extracted with DCM (3×). The combined organic layers were dried over Na$_2$SO$_4$, filtered and concentrated. Chromatography (30% EtOAc/hexanes) gave 12A as an oil.

Steps 2-3

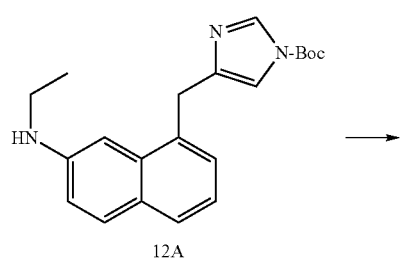

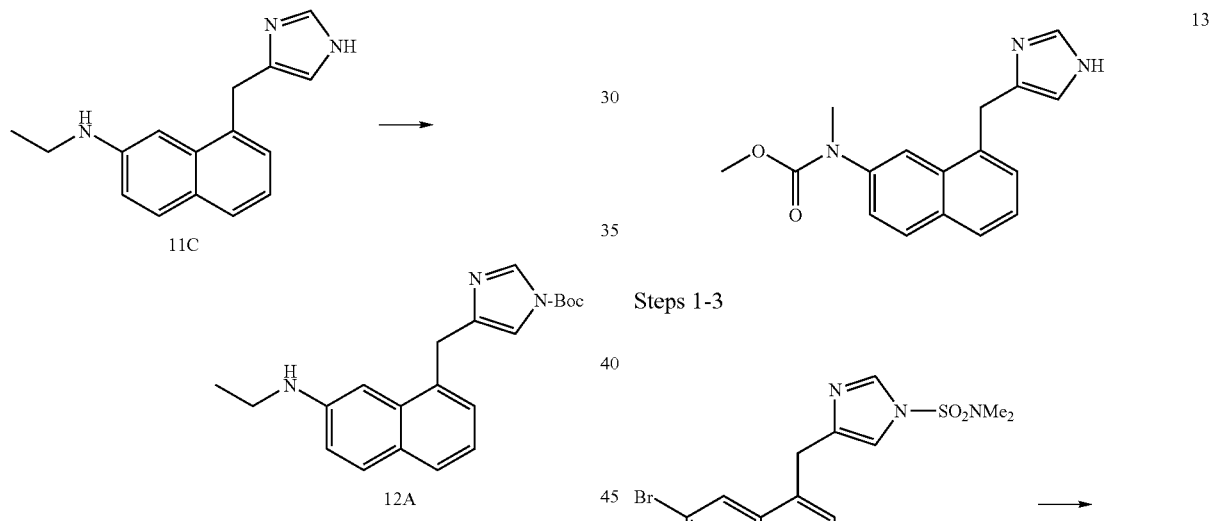

In a manner similar to that described in Example 7, 10B was reacted with MeNCO in DCM to provide 12B.

A solution of compound 12B in DCM (5 mL) was treated with TFA (0.5 mL), stirred at RT for 30 min, and concentrated. Chromatography (5-10% of 7N NH$_3$-MeOH in DCM) provided the title compound 12 as a white foam. LCMS m/z=309 (MH+).

Example 13

Steps 1-3

In a manner analogous to that described in Example 11 (Steps 3-4), 11A was sequentially reacted with CuI/methylamine and deprotected with HCl to provide 13A. LCMS m/z=238 (MH+).

Compound 13A was then reacted with ClCO$_2$Me/DMAP as described in Example 11 (Step 5). LCMS m/z=296 (MH+).

Example 14

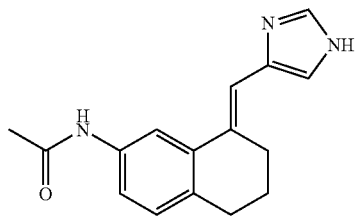

14

Step 1

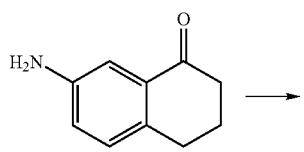

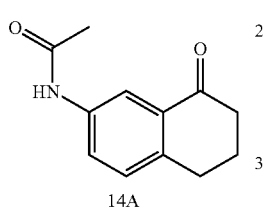

14A

7 Amino-1-tetralone (5.07 g, 31.45 mmol) and anhydrous Et₃N (5.6 mL, 40 mmol) were dissolved in anhydrous DCM (50 mL) and cooled in ice bath. Acetyl chloride (2.5 mL; 35 mmol) was added slowly dropwise. After the addition, the cooling bath was removed and the solution stirred at RT for 6 h. The mixture was then diluted with DCM, washed with water, and dried over Na₂SO₄. The mixture was purified by flash chromatography (SiO₂, 0-10% MeOH/DCM) to afford 14A (4.45 g). LCMS m/z=204 (MH+).

Step 2

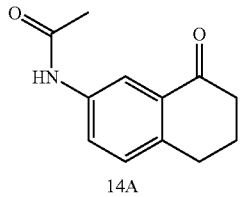 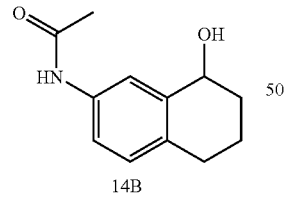

14A    14B 7-acetamido-1-tetralone (14A, 4.45 g, 21.89 mmol) was dissolved in DCM (50 mL) and MeOH (150 mL) and cooled in ice bath. Solid NaBH₄ (0.95 g, 25 mmol) was added in small portions, under N₂, over a period of 1 h. The cooling bath was then removed, and the mixture stirred at RT for two more hours. After quenching the reaction with water (60 mL), the solvents were removed in vacuo. The resulting residue was taken in DCM, washed with water, and dried over anhydrous Na₂SO₄. The mixture was purified by flash chromatography (SiO₂, 0-10% MeOH/DCM) to provide 14B gradient (2.64 g). LCMS m/z=206 (MH+).

Step 3

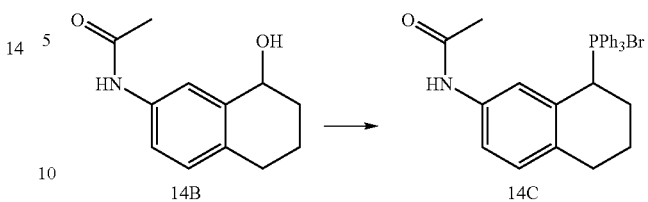

14B    14C

A suspension of 14B (2.4 g, 11.69 mmol) in anhydrous CH₃CN (35 mL) was treated with PPh₃-HBr (4.12 g) and heated to reflux under nitrogen for 6 h. After cooling to RT, the solvent was removed in vacuo. The resulting dark foam was stirred for 1 h with Et₂O (60 mL). The ether supernatant was discarded. This process was repeated five times to afford 14C (precipitate).

Step 4

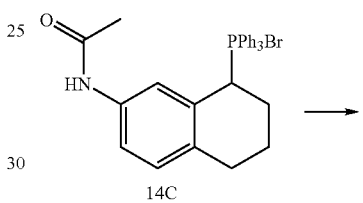

14C

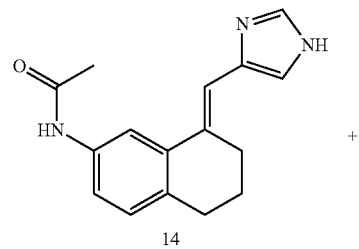

14

+

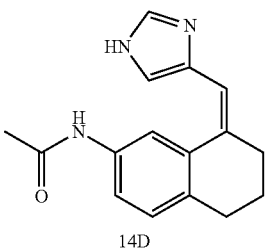

14D

In a two-necked flask, imidazole-4-carboxyaldehyde (0.45 g, 4.66 mmol) was suspended in absolute EtOH (7.0 mL) and warmed to 65° C. A solution of KOtBu (1.0 M/THF, 4.7 mL) was added dropwise. After the addition, the solution was stirred for another 15 min and then cannulated into another two-necked flask containing a mixture of 14C (1.03 g, 1.94 mmol) in absolute EtOH (10 mL) at 80° C. under N₂. The resulting mixture was heated to reflux for 19 h. After cooling to RT, the solvents were removed in vacuo. The residue was treated with water and extracted with DCM. The combined extracts were washed with water and dried over anhydrous Na₂SO₄. The products were purified twice by flash chromatography (SiO₂, 0-10% MeOH/DCM). Final separation and purification was achieved by preparative TLC (eluted twice with 5% NH₃—MeOH in DCM) to provide compound 14 (LCMS m/z=268, MH+) and 14D (LCMS m/z=268, MH+).

Example 15

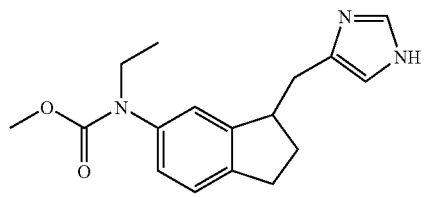

Step 1

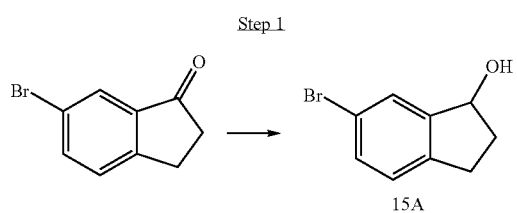

In a manner similar to that described in Example 14 (Step 2), 6-Bromo-1-indanone (11g) was treated with NaBH₄ to provide 15A in nearly quantitative yield. The product was used in the next step without chromatographic purification.
Step 2

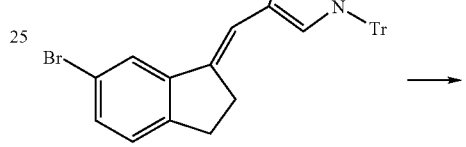

A mixture of 15A (11 g, 51.6 mmol) and Ph₃P—HBr (17.7 g, 51.6 mmol) in benzene (35 mL) was heated at 90° C. overnight. After cooling to RT, the solid was filtered and dried in vacuo. The solid was washed with Et₂O and acetone, and then vacuum dried to afford 15B (18.9 g, 68%).
Step 3

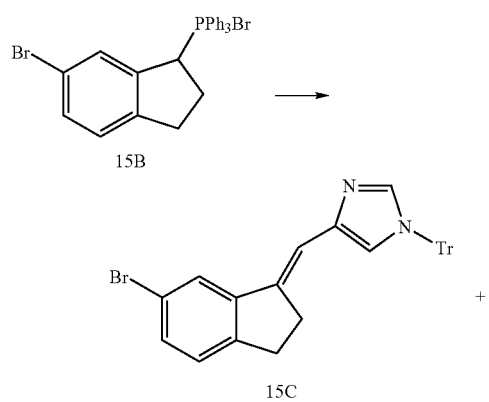

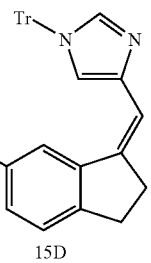

15D

A mixture of the phosphonium salt 15B (5.38 g, 10 mmol), 1-trityl-imidazole-4-carbaldehyde (3.55 g, 10.5 mmol), K₂CO₃ (13.8 g, 100 mmol), and catalytic 18-crown-6 in DCM (50 mL) was refluxed overnight. The reaction was cooled, treated with water and extracted with DCM. The organic layer was dried over anhydrous Na₂SO₄, concentrated, and purified by flash chromatography to afford compounds 15C and 15D.
Step 4

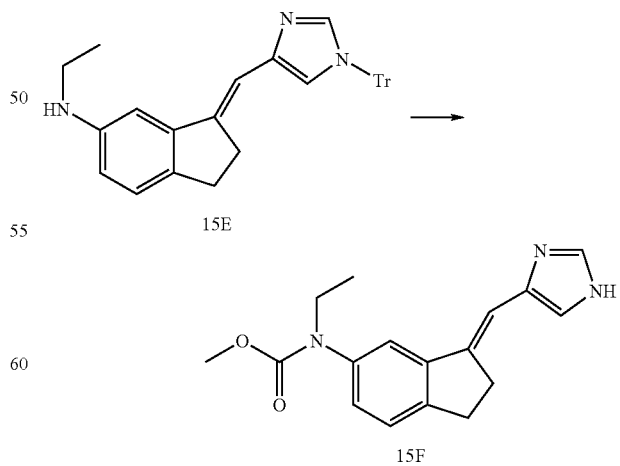

In a manner similar to that described in Example 11 (Step 3), 15C was treated with K₃PO₄ (2 eq), CuI (0.3 eq), EtNH₂, (3 eq.) and 2-acetylcyclohexanone (0.3 eq) in DMF to provide 15E as a cream colored solid (72% yield).
Steps 5-7

In a manner similar to that described in Example 1 (Steps 6-7), compound 15E was sequentially treated with ClCO₂Me and TFA/Et₃SiH to provide 15F as a brown colored solid (74% overall yield). LCMS m/z=298 (MH+).

Compound 15F (40 mg, 0.13 mmol) was dissolved in EtOH (20 mL) under an atmosphere of N₂ and then treated with 10% Pd/C (40 mg). The mixture was hydrogenated overnight (40 psi H₂), filtered through a pad of celite and concentrated. Column chromatography (7N NH₃-MeOH in DCM) provided the title compound 15 as brown colored solid (90% yield). LCMS m/z=300 (MH+).

In a similar manner (Steps 4-6), compound 15D was converted to 10G. LCMS m/z 298 (MH+).

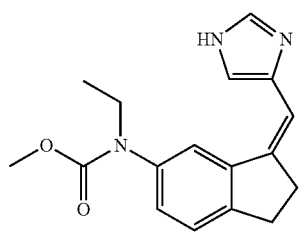

Example 16

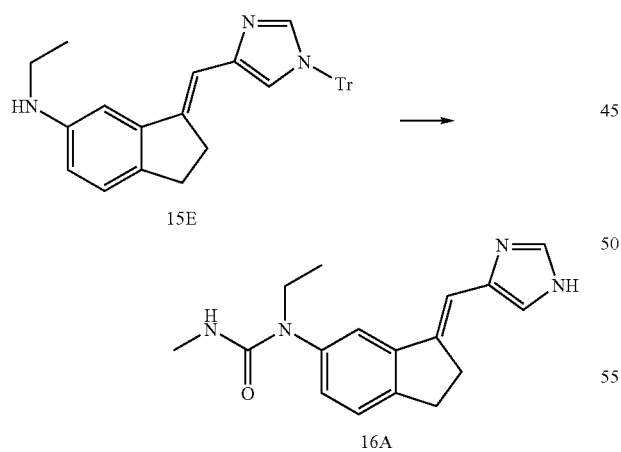

In a manner analogous to that described previously (Example 7 and Example 15, Step 6), compound 15E was sequentially treated with MeNCO and then deprotected with TFA/Et₃SiH to provide 16A as a cream colored solid (80% overall yield). LCMS m/z 297 (MH+).

In a similar manner to that described in Example 15 (Step 7), 16A was hydrogenated to provide the title compound 16 as a brown colored solid (87% yield). LCMS m/z 299 (MH+).

Assay:

Efficacy agonist activity values (Emax, GTPγS assay) for α2A and α2C were determined by following the general procedure detailed by Umland et. al ("Receptor reserve analysis of the human α₂c-adrenoceptor using [³⁵S]GTPγS and cAMP functional assays" European Journal of Pharmacology 2001, 411, 211-221). For the purposes of the present invention, a compound is defined to be a specific or at least selective agonist of the α2C receptor subtype if the compound's efficacy at the α2C receptor is ≧30% Emax (GTPγS assay) and its efficacy at the α2A receptor is ≦35% Emax (GTPγS assay).

The following compounds were evaluated to be specific or at least selective agonists of the α2C receptor subtype based on the previously defined definition: 1, 7D, 7E, 7F, 7I, 9, 10, 11, 11D, 12 and 14. While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound of the structure:

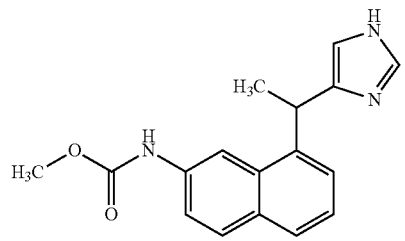

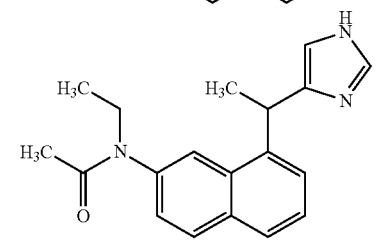

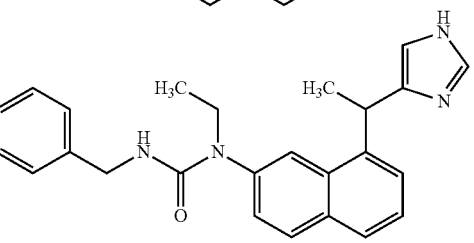

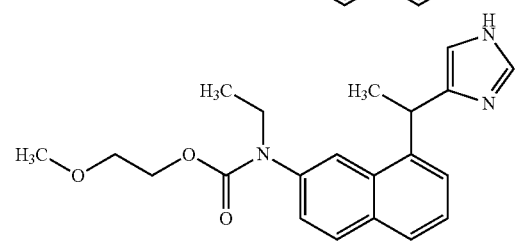

75
-continued
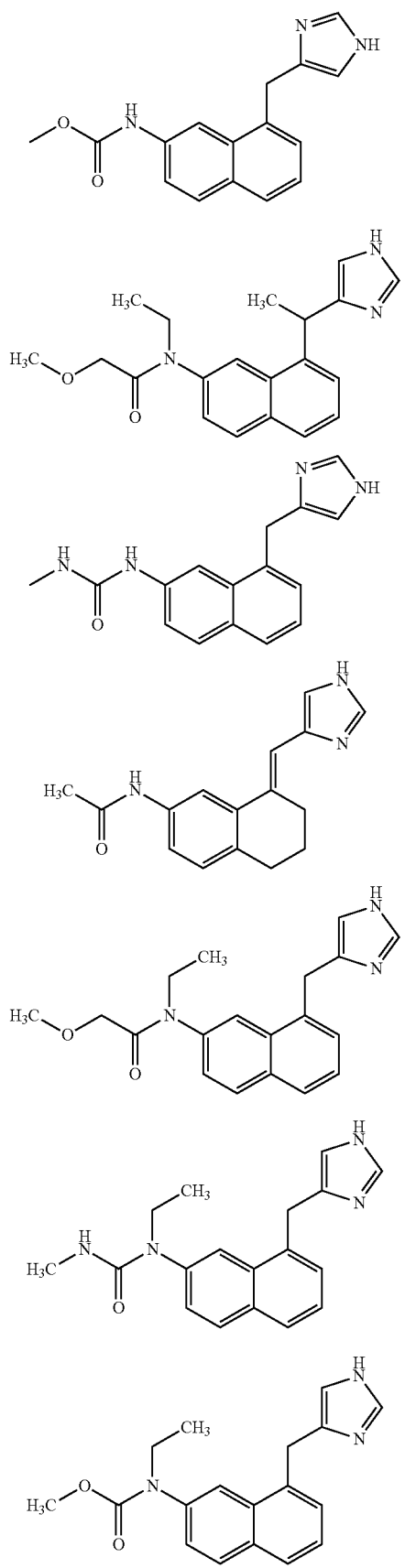
76
-continued
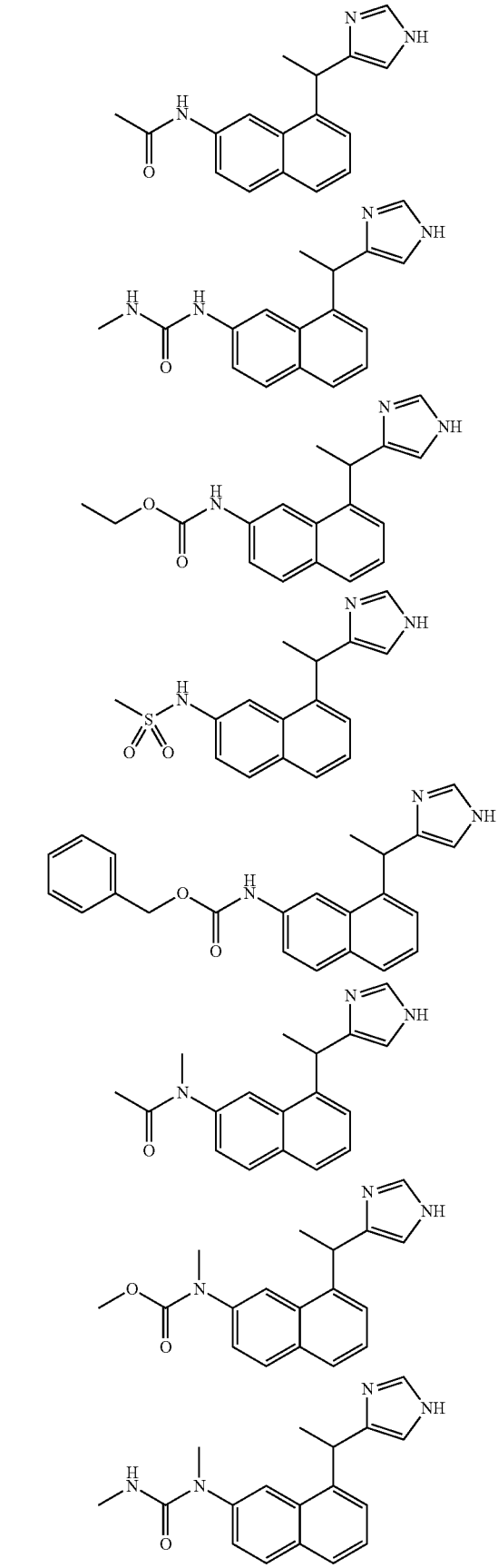

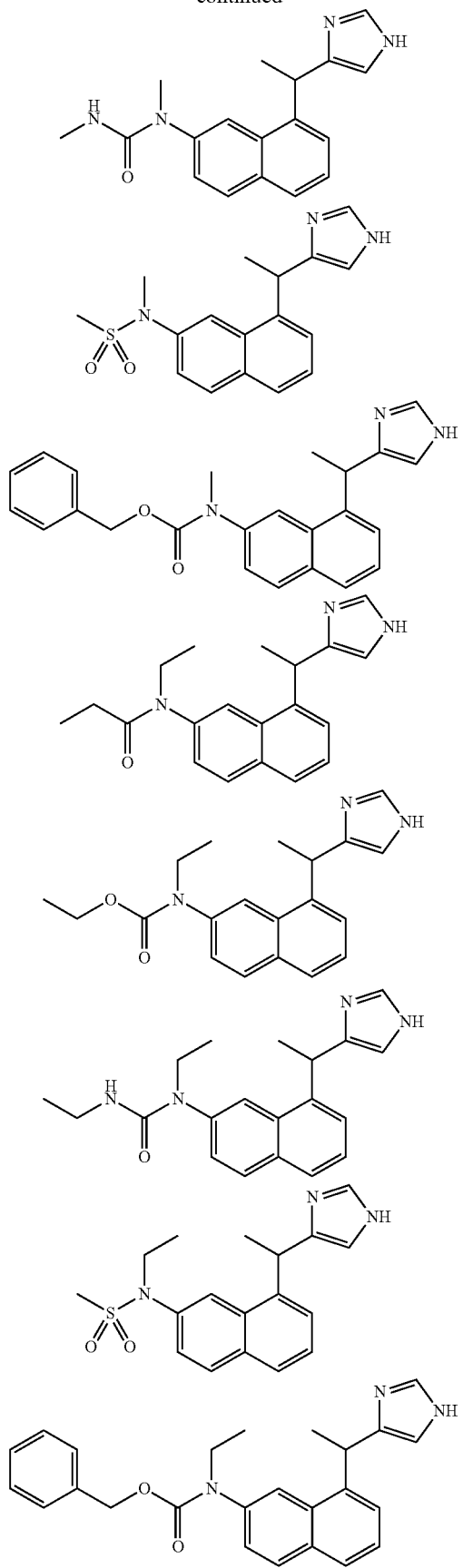
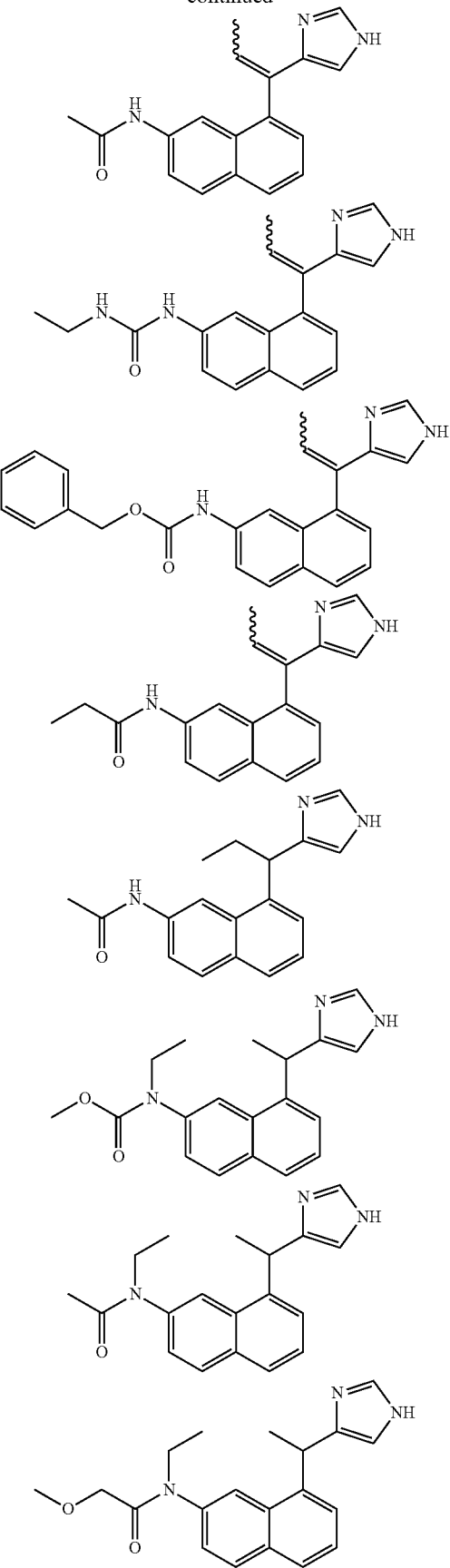

-continued

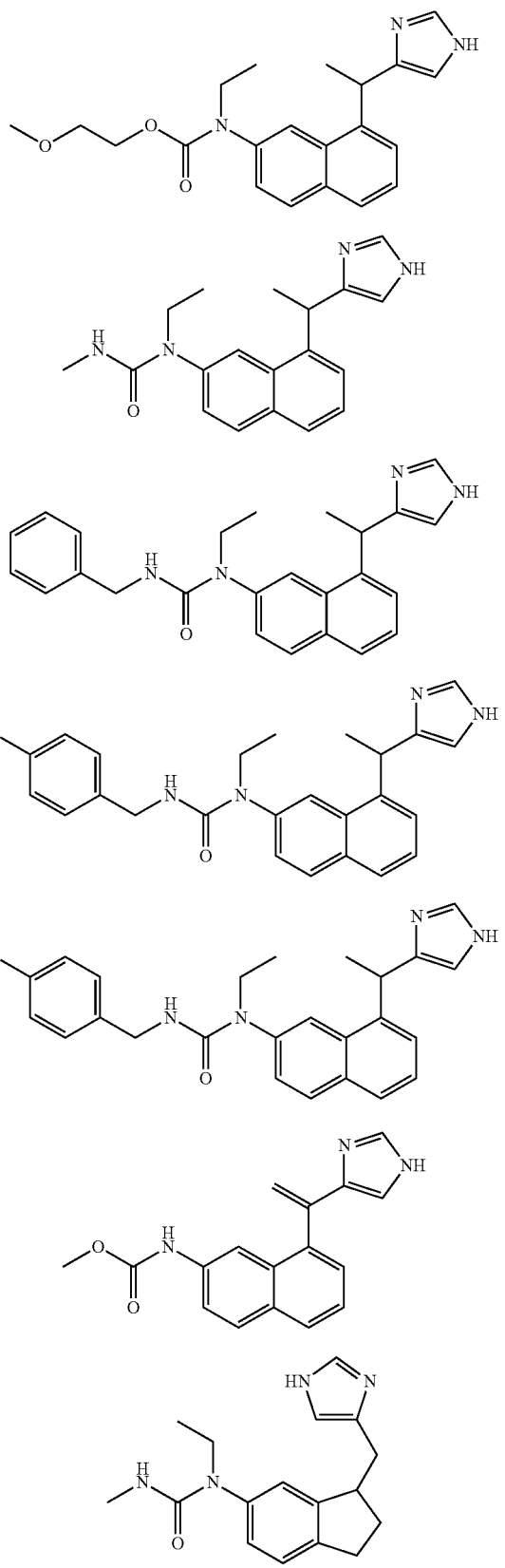

-continued

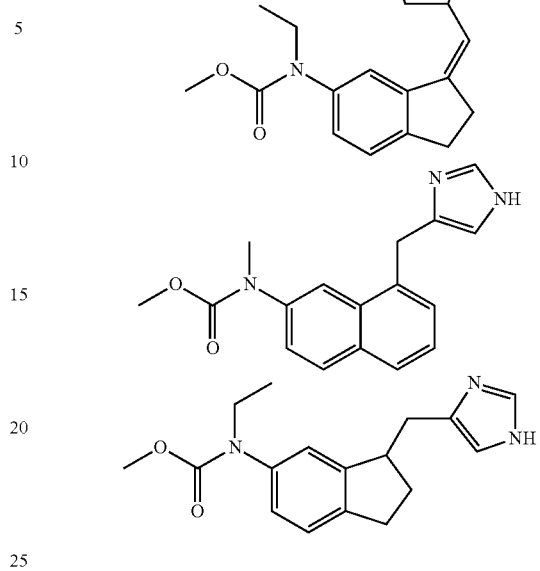

or a pharmaceutically acceptable salt thereof.

2. A pharmaceutical composition comprising at least one compound of claim 1, or a pharmaceutically acceptable salt thereof and at least one pharmaceutically acceptable carrier, adjuvant or vehicle.

3. The pharmaceutical composition of claim 2, further comprising one or more additional therapeutic agents.

4. The pharmaceutical composition of claim 3, wherein said additional therapeutic agents are selected from the group consisting of steroids, PDE-4 inhibitors, anti-muscarinic agents, cromolyn sodium, $H_1$ receptor antagonists, $5\text{-}HT_1$ agonists, NSAIDs, angiotensin-converting enzyme inhibitors, angiotensin II receptor agonists, β-blockers, β-agonists, leukotriene antagonists, diuretics, aldosterone antagonists, ionotropic agents, natriuretic peptides, pain management agents, anti-anxiety agents, anti-migraine agents, and therapeutic agents suitable for treating heart conditions, psychotic disorders, and glaucoma.

5. A method for treating one or more conditions associated with α2C adrenergic receptors, comprising administering to a mammal in need of such treatment a compound of claim 1 or a pharmaceutically acceptable salt thereof, wherein the conditions are selected from the group consisting of allergic rhinitis, congestion, pain, diarrhea, glaucoma, congestive heart failure, cardiac ischemia, manic disorders, depression, anxiety, migraine, stress-induced urinary incontinence, neuronal damage from ischemia and schizophrenia.

6. The method of claim 5, wherein the condition is congestion.

7. The method of claim 6, wherein the congestion is associated with perennial allergic rhinitis, seasonal allergic rhinitis, non-allergic rhinitis, vasomotor rhinitis, rhinitis medicamentosa, sinusitis, acute rhinosinusitis, or chronic rhinosinusitis.

8. The method of claim 7 wherein the congestion is caused by polyps or is associated with the common cold.

9. The method of claim 5, wherein the condition is pain.

10. The method of claim 9, wherein the pain is associated with neuropathy, inflammation, arthritis, or diabetes.

* * * * *